(12) United States Patent  
Ishisone et al.

(10) Patent No.: US 9,368,741 B2  
(45) Date of Patent: Jun. 14, 2016

(54) LIGHT-EMITTING ELEMENT, LIGHTING DEVICE, LIGHT-EMITTING DEVICE, AND ELECTRONIC DEVICE

(71) Applicant: SEMICONDUCTOR ENERGY LABORATORY CO., LTD., Kanagawa-ken (JP)

(72) Inventors: Takahiro Ishisone, Kanagawa (JP); Satoshi Seo, Kanagawa (JP)

(73) Assignee: Semiconductor Energy Laboratory Co., Ltd. (JP)

(*) Notice: Subject to any disclaimer, the term of this patent is extended or adjusted under 35 U.S.C. 154(b) by 219 days.

(21) Appl. No.: 14/276,467

(22) Filed: May 13, 2014

(65) Prior Publication Data

US 2014/0340888 A1 Nov. 20, 2014

(30) Foreign Application Priority Data

May 17, 2013 (JP) ................................ 2013-104880

(51) Int. Cl.
  *H01L 33/00* (2010.01)
  *H01L 51/50* (2006.01)
  *H01L 51/00* (2006.01)

(52) U.S. Cl.
  CPC .......... *H01L 51/504* (2013.01); *H01L 51/5016* (2013.01); *H01L 51/006* (2013.01); *H01L 51/0067* (2013.01); *H01L 51/0072* (2013.01); *H01L 51/0085* (2013.01)

(58) Field of Classification Search
  CPC . H01L 51/006; H01L 51/504; H01L 51/0067; H01L 51/0072; H01L 51/0085; H01L 51/5016
  See application file for complete search history.

(56) References Cited

U.S. PATENT DOCUMENTS

| | | |
|---|---|---|
| 6,911,271 B1 | 6/2005 | Lamansky et al. |
| 6,939,624 B2 | 9/2005 | Lamansky et al. |
| 7,009,338 B2 | 3/2006 | D'Andrade et al. |
| 7,285,907 B2 | 10/2007 | D'Andrade et al. |
| 7,381,479 B2 | 6/2008 | Lamansky et al. |
| 7,553,560 B2 | 6/2009 | Lamansky et al. |
| 7,771,844 B2 | 8/2010 | Inoue et al. |
| 7,943,925 B2 | 5/2011 | Yamazaki |
| 8,564,190 B2 | 10/2013 | Seo et al. |
| 8,653,553 B2 | 2/2014 | Yamazaki et al. |

(Continued)

FOREIGN PATENT DOCUMENTS

| | | |
|---|---|---|
| JP | 2004-522276 | 7/2004 |
| WO | WO-2008/132965 | 11/2008 |

*Primary Examiner* — Stephen F Husar
(74) *Attorney, Agent, or Firm* — Husch Blackwell LLP

(57) ABSTRACT

A light-emitting element includes a first electrode; a first light-emitting layer over the first electrode, containing a first phosphorescent compound and a first host material; a second light-emitting layer over the first light-emitting layer, containing a second phosphorescent compound and a second host material; a third light-emitting layer over the second light-emitting layer, containing a third phosphorescent compound and a third host material; and a second electrode over the third light-emitting layer. Between peaks of emission spectra of the first, second, and third phosphorescent compounds, the peak of the emission spectrum of the second phosphorescent compound is on the longest wavelength side and that of the emission spectrum of the third phosphorescent compound is on the shortest wavelength side. The third host material has higher triplet excitation energy than the first host material and the second host material.

30 Claims, 14 Drawing Sheets

(56) References Cited

U.S. PATENT DOCUMENTS

| | | | |
|---|---|---|---|
| 8,916,897 B2 * | 12/2014 | Yamazaki | 257/98 |
| 9,099,617 B2 * | 8/2015 | Yamazaki | H01L 33/504 |
| 2005/0074630 A1 | 4/2005 | Kanno et al. | |
| 2005/0106415 A1 | 5/2005 | Jarikov et al. | |
| 2010/0127246 A1 | 5/2010 | Nakayama et al. | |
| 2011/0057178 A1 | 3/2011 | Shitagaki et al. | |
| 2011/0210316 A1 | 9/2011 | Kadoma et al. | |
| 2012/0205632 A1 | 8/2012 | Shitagaki et al. | |
| 2012/0205687 A1 | 8/2012 | Yamazaki et al. | |
| 2012/0217486 A1 | 8/2012 | Takemura et al. | |
| 2012/0217487 A1 | 8/2012 | Yamazaki et al. | |

* cited by examiner

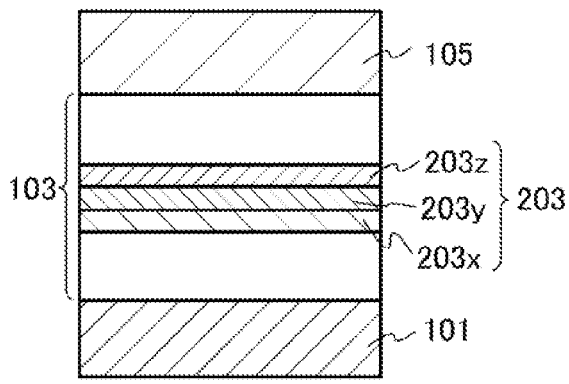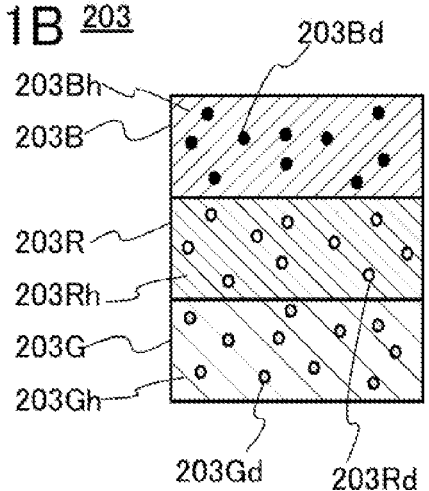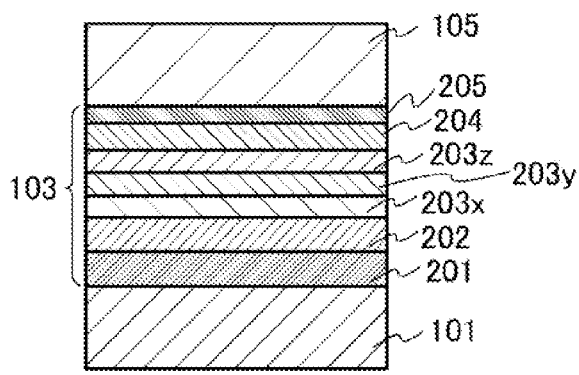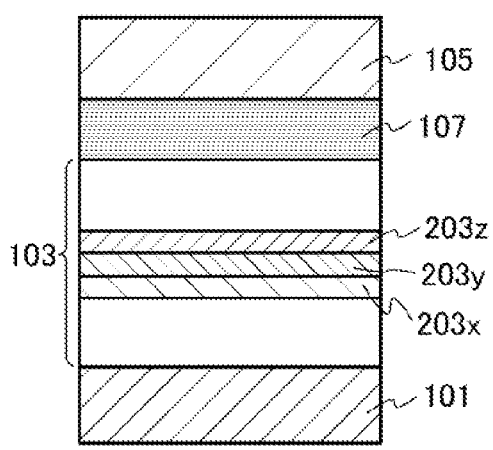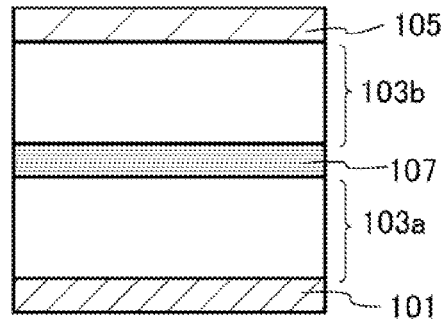

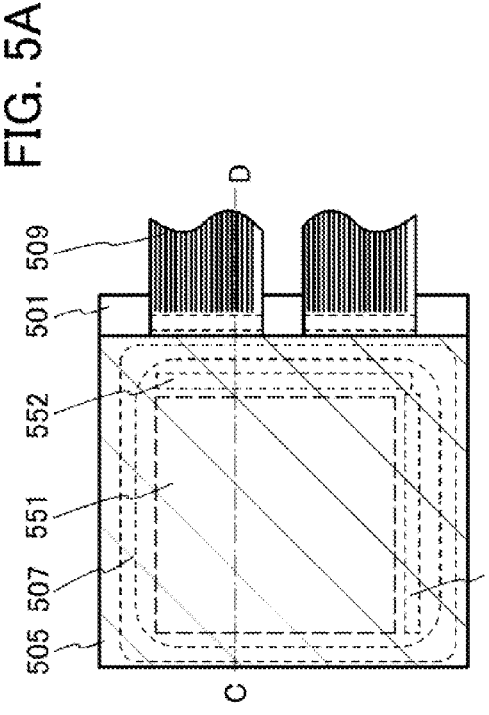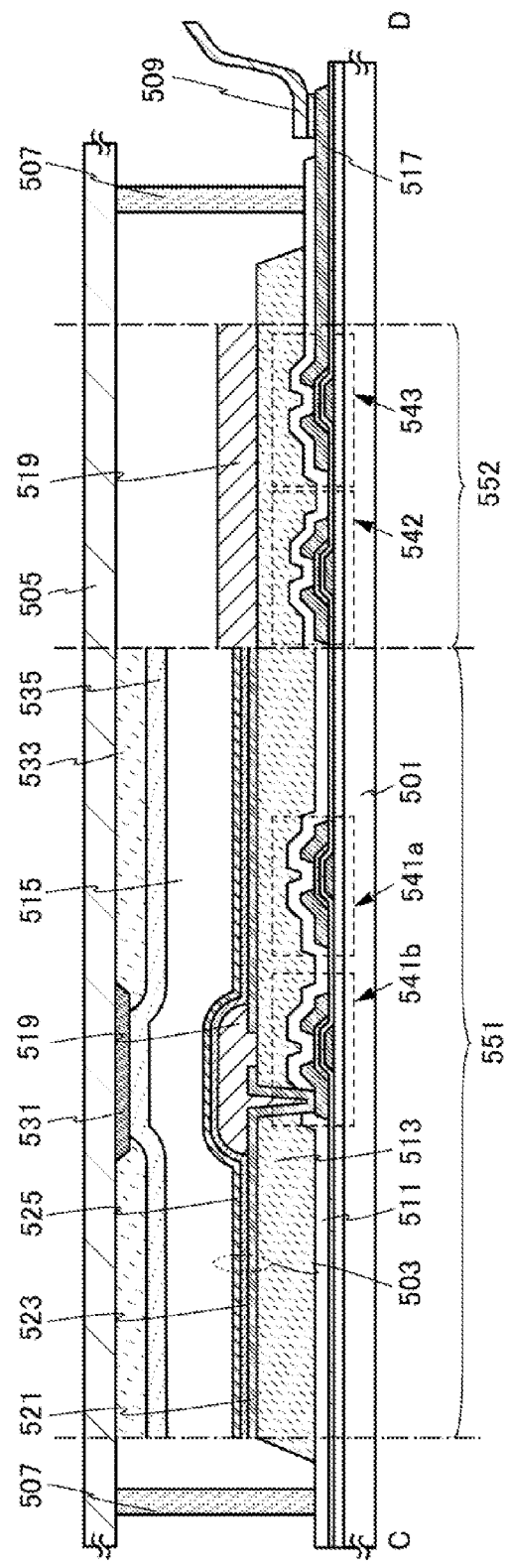

LIGHT-EMITTING ELEMENT, LIGHTING DEVICE, LIGHT-EMITTING DEVICE, AND ELECTRONIC DEVICE

BACKGROUND OF THE INVENTION

1. Field of the Invention

The present invention relates to a light-emitting element, a lighting device, a light-emitting device, and an electronic device. In particular, the present invention relates to a light-emitting element, a lighting device, a light-emitting device, and an electronic device utilizing electroluminescence (EL).

2. Description of the Related Art

Research and development have been extensively conducted on light-emitting elements utilizing EL. In a basic structure of the light-emitting element, a layer containing a light-emitting organic compound (hereinafter also referred to as an EL layer) is sandwiched between a pair of electrodes. The light-emitting element utilizing EL has attracted attention as a next-generation flat panel display element owing to characteristics such as feasibility of being thinner and lighter, high-speed response to input signals, and capability of direct current low voltage driving. In addition, a display using the light-emitting element has a feature that it is excellent in contrast and image quality, and has a wide viewing angle. Further, since the light-emitting element is a plane light source, application of the light-emitting element as a light source such as a backlight of a liquid crystal display and an illumination device is proposed.

In the case of a light-emitting element in which a layer containing an organic compound used as a light-emitting substance is provided between a pair of electrodes, by applying a voltage to the element, electrons from a cathode and holes from an anode are injected into the layer containing the organic compound and thus a current flows. The injected electrons and holes then lead the organic compound to its excited state, so that light emission is obtained from the excited organic compound.

As the excited state caused by an organic compound, there are a singlet excited state (S*) and a triplet excited state (T*). Light emission from a singlet excited state is referred to as fluorescence and light emission from a triplet excited state is referred to as phosphorescence. Here, in a compound that emits fluorescence (hereinafter also referred to as a fluorescent compound), in general, phosphorescence is not observed at room temperature, and only fluorescence is observed. Accordingly, the internal quantum efficiency (the ratio of generated photons to injected carriers) of a light-emitting element including the fluorescent compound is assumed to have a theoretical limit of 25% based on the ratio of the singlet excited state to the triplet excited state.

Meanwhile, when a compound that emits phosphorescence (hereinafter also referred to as a phosphorescent compound) is used, the internal quantum efficiency can be theoretically increased to 100%. That is, higher emission efficiency can be obtained than using a fluorescent compound. For these reasons, a light-emitting element including a phosphorescent compound has been actively developed in recent years in order to obtain a light-emitting element with high emission efficiency.

Patent Document 1 discloses a light-emitting element including a blue light-emitting layer and an orange light-emitting layer that use phosphorescent materials.

REFERENCE

Patent Document

[Patent Document 1] United States Patent Application Publication No. 2005/0074630

SUMMARY OF THE INVENTION

Although an internal quantum efficiency of 100% in a phosphorescent compound is theoretically possible, such high efficiency can be hardly achieved without optimization of an element structure or a combination with another material. Especially in a light-emitting element which includes a plurality of kinds of phosphorescent compounds having different bands (different emission colors) as light-emitting substances, it is difficult to obtain highly efficient light emission without not only considering energy transfer but also optimizing the efficiency of the energy transfer.

In a multicolor light-emitting element using a plurality of kinds of light-emitting substances exhibiting different emission colors, beside improvement of emission efficiency, it is also necessary to attain a good balance between light emissions by the light-emitting substances that exhibit different emission colors. It is not easy to keep a balance between light emissions by the light-emitting substances and to achieve high emission efficiency at the same time.

In view of the above, an object of one embodiment of the present invention is to provide a light-emitting element in which a good balance between light emissions by a plurality of light-emitting substances is achieved. An object of one embodiment of the present invention is to provide a light-emitting element with high emission efficiency. An object of one embodiment of the present invention is to provide a light-emitting element with high reliability.

An object of one embodiment of the present invention is to provide a light-emitting device, an electronic device, and a lighting device each having reduced power consumption by using the above light-emitting element. An object of one embodiment of the present invention is to provide a light-emitting device, an electronic device, and a lighting device each having high reliability by using the above light-emitting element.

In one embodiment of the present invention, there is no need to achieve all the above objects.

One embodiment of the present invention is a light-emitting element that includes a first electrode; a first light-emitting layer over the first electrode, containing a first phosphorescent compound and a first host material; a second light-emitting layer over the first light-emitting layer, containing a second phosphorescent compound and a second host material; a third light-emitting layer over the second light-emitting layer, containing a third phosphorescent compound and a third host material; and a second electrode over the third light-emitting layer. Between a peak of an emission spectrum of the first phosphorescent compound, a peak of an emission spectrum of the second phosphorescent compound, and a peak of an emission spectrum of the third phosphorescent compound, the peak of the emission spectrum of the second phosphorescent compound is on the longest wavelength side and the peak of the emission spectrum of the third phosphorescent compound is on the shortest wavelength side. The third host material has higher triplet excitation energy than the first host material and the second host material.

In the above structure, it is preferable that the first phosphorescent compound emit green light, the second phosphorescent compound emit red light, and the third phosphorescent compound emit blue light.

Note that in the present specification, a phosphorescent compound emitting green light has an emission peak at greater than or equal to 520 nm and less than 600 nm; a phosphorescent compound emitting red light has an emission peak at greater than or equal to 600 nm and less than or equal to 750 nm; and a phosphorescent compound emitting blue light has an emission peak at greater than or equal to 440 nm and less than 520 nm.

In any of the above structures, it is preferable that the first host material, the second host material, and the third host material each have an electron-transport property. Alternatively, it is preferable that the first host material, the second host material, and the third host material each have a hole-transport property. Further alternatively, it is preferable that the first host material, the second host material, and the third host material each have an electron-transport property and a hole-transport property.

In any of the above structures, it is preferable that the first host material, the second host material, and the third host material each have a hole-transport skeleton and an electron-transport skeleton. The host materials may have different hole-transport skeletons and electron-transport skeletons or the same hole-transport skeleton and electron-transport skeleton.

In any of the above structures, it is preferable that the first host material be the same as the second host material.

In any of the above structures, it is preferable that the first light-emitting layer also contain a first carrier-transport compound, one of the first host material and the first carrier-transport compound be a hole-transport compound, and the other of the first host material and the first carrier-transport compound be an electron-transport compound.

In any of the above structures, it is preferable that the second light-emitting layer also contain a second carrier-transport compound, one of the second host material and the second carrier-transport compound be a hole-transport compound, and the other of the second host material and the second carrier-transport compound be an electron-transport compound.

In any of the above structures, it is preferable that the third light-emitting layer also contain a third carrier-transport compound, one of the third host material and the third carrier-transport compound be a hole-transport compound, and the other of the third host material and the third carrier-transport compound be an electron-transport compound.

In any of the above structures, it is preferable that the second light-emitting layer have a thickness greater than or equal to 2 nm and less than or equal to 20 nm, preferably greater than or equal to 5 nm and less than or equal to 10 nm.

In any of the above structures, it is preferable that the second light-emitting layer be in contact with the first light-emitting layer and the third light-emitting layer. Specifically, one embodiment of the present invention is a light-emitting element that includes a first electrode; a first light-emitting layer over the first electrode, containing a first phosphorescent compound and a first host material; a second light-emitting layer on and in contact with the first light-emitting layer, containing a second phosphorescent compound and a second host material; a third light-emitting layer on and in contact with the second light-emitting layer, containing a third phosphorescent compound and a third host material; and a second electrode over the third light-emitting layer. Between a peak of an emission spectrum of the first phosphorescent compound, a peak of an emission spectrum of the second phosphorescent compound, and a peak of an emission spectrum of the third phosphorescent compound, the peak of the emission spectrum of the second phosphorescent compound is on the longest wavelength side and the peak of the emission spectrum of the third phosphorescent compound is on the shortest wavelength side. The third host material has higher triplet excitation energy than the first host material and the second host material.

In any of the above structures, the first carrier-transport compound and the second carrier-transport compound may be the same material.

Note that a light-emitting device, a lighting device, and an electronic device each including a light-emitting element with any of the above structures are also embodiments of the present invention.

Note that the light-emitting device in this specification includes, in its category, a display device using a light-emitting element. Further, the category of the light-emitting device in this specification includes a module in which a light-emitting device is provided with a connector such as an anisotropic conductive film or a tape carrier package (TCP); a module having a TCP at the tip of which a printed wiring board is provided; and a module in which an integrated circuit (IC) is directly mounted on a light-emitting device by a chip on glass (COG) method. Furthermore, the category includes a light-emitting device which is used in lighting equipment or the like.

In one embodiment of the present invention, a light-emitting element in which a good balance between light emissions by a plurality of light-emitting substances is achieved can be provided. In one embodiment of the present invention, a light-emitting element with high emission efficiency can be provided. In one embodiment of the present invention, a light-emitting element with high reliability can be provided.

In one embodiment of the present invention, a light-emitting device, an electronic device, or a lighting device having reduced power consumption by using the above light-emitting element can be provided. In one embodiment of the present invention, a light-emitting device, an electronic device, or a lighting device having high reliability by using the above light-emitting element can be provided.

BRIEF DESCRIPTION OF THE DRAWINGS

FIGS. 1A to 1E illustrate examples of a light-emitting element of one embodiment of the present invention.

FIGS. 5A and 5B illustrate an example of a light-emitting device of one embodiment of the present invention.

DETAILED DESCRIPTION OF THE INVENTION

Figure 2A:
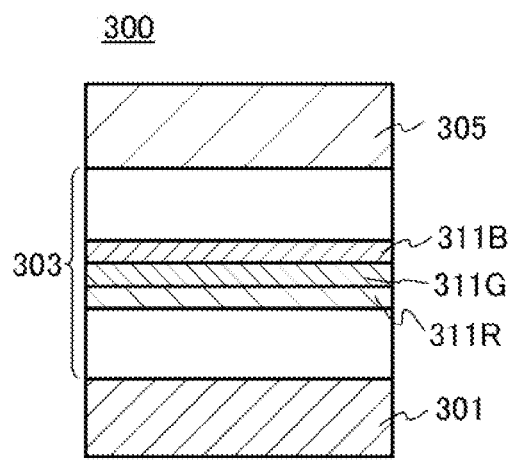
FIGS. 2A and 2B illustrate an example of a comparative light-emitting element.

Embodiments will be described in detail with reference to drawings. Note that the present invention is not limited to the description below, and it is easily understood by those skilled in the art that various changes and modifications can be made without departing from the spirit and scope of the present invention. Therefore, the present invention should not be construed as being limited to the description in the following embodiments.

Note that in the structures of the invention described below, the same portions or portions having similar functions are denoted by the same reference numerals in different drawings, and description of such portions is not repeated. Further, the same hatching pattern is applied to portions having similar functions, and the portions are not especially denoted by reference numerals in some cases.

In addition, the position, size, range, or the like of each structure illustrated in drawings and the like is not accurately represented in some cases for easy understanding. Therefore, the disclosed invention is not necessarily limited to the position, the size, the range, or the like disclosed in the drawings and the like.

Embodiment 1

In this embodiment, light-emitting elements of embodiments of the present invention will be described with reference to FIGS. 1A to 1E, FIGS. 2A and 2B, and FIGS. 3A and 3B.

A point of one embodiment of the present invention is to use three kinds of phosphorescent compounds whose emission spectra have peaks at different wavelengths and to make all the three kinds of phosphorescent compounds emit light with high efficiency, thereby improving emission efficiency and a lifetime of a multicolor light-emitting element.

In a general method for obtaining a multicolor light-emitting element including a phosphorescent compound, a plurality of kinds of phosphorescent compounds whose emission spectra have peaks at different wavelengths are dispersed in some host material in an appropriate ratio. However, in such a method, the phosphorescent compound that emits light of the longest wavelength easily emits light, so that it is extremely difficult to design and control an element structure (especially the concentrations of the phosphorescent compounds in the host material) for obtaining polychromatic light.

Another technique for obtaining a multicolor light-emitting element is what is called a tandem structure. In a tandem structure, light-emitting elements whose emission spectra have peaks at different wavelengths are stacked in series. For example, a blue light-emitting element, a green light-emitting element, and a red light-emitting element are stacked in series and made to emit light at the same time, whereby polychromatic light (in this case, white light) can be easily obtained. The element structure can be relatively easily designed and controlled because the blue light-emitting element, the green light-emitting element, and the red light-emitting element can be independently optimized. However, the stacking of three elements is accompanied by an increase in number of layers and makes the fabrication complicated. In addition, when a problem occurs in electrical contact at connection portions between the elements (what is called intermediate layers), an increase in drive voltage, i.e., power loss might be caused.

<<Comparative Light-Emitting Element>>

A comparative light-emitting element 300 illustrated in FIG. 2A includes a first electrode 301, an EL layer 303 over the first electrode 301, and a second electrode 305 over the EL layer 303. One of the first electrode 301 and the second electrode 305 serves as an anode and the other serves as a cathode. In this embodiment, the first electrode 301 serves as an anode and the second electrode 305 serves as a cathode.

When a voltage higher than the threshold voltage of the light-emitting element is applied between the first electrode 301 and the second electrode 305, holes are injected from the first electrode 301 side to the EL layer 303 and electrons are injected from the second electrode 305 side to the EL layer 303. The injected electrons and holes are recombined in the EL layer 303 and a light-emitting substance contained in the EL layer 303 emits light.

Figure 2B:
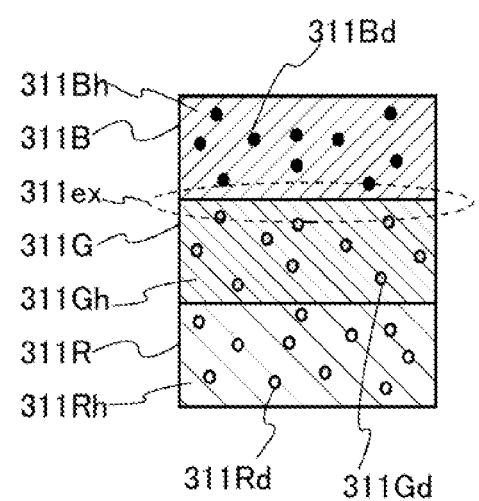

As illustrated in FIG. 2B, the EL layer 303 includes, from the first electrode 301 side, a red light-emitting layer 311R containing a phosphorescent compound 311Rd emitting red light and a host material 311Rh; a green light-emitting layer 311G containing a phosphorescent compound 311Gd emitting green light and a host material 311Gh; and a blue light-emitting layer 311B containing a phosphorescent compound 311Bd emitting blue light and a host material 311Bh. The phosphorescent compounds contained in the light-emitting layers are dispersed in the respective host materials and isolated from each other by the host materials.

In that case, between the phosphorescent compounds, energy transfer by electron exchange interaction (what is called Dexter mechanism) is suppressed. In other words, the excitation energy of the phosphorescent compound 311Bd emitting blue light is not easily transferred by the Dexter mechanism to the phosphorescent compound 311Gd emitting green light or the phosphorescent compound 311Rd emitting red light. Furthermore, the excitation energy of the phosphorescent compound 311Gd emitting green light is not easily transferred by the Dexter mechanism to the phosphorescent compound 311Rd emitting red light. Thus, a phenomenon in which the phosphorescent compound 311Rd emitting light of the longest wavelength mainly emits light is suppressed. A carrier recombination region 311ex in the light-emitting element 300 is formed in the blue light-emitting layer 311B or in the vicinity of an interface between the blue light-emitting layer 311B and the green light-emitting layer 311G (in other words, the phosphorescent compound 311Bd emitting blue light is mainly excited). As a result, excitons are prevented from being directly generated in the red light-emitting layer 311R, whereby the phosphorescent compound 311Rd emitting red light is prevented from mainly emitting light.

Note that if energy transfer from the phosphorescent compound 311Bd emitting blue light is completely inhibited, in turn, light emission from the phosphorescent compound 311Rd emitting red light cannot be obtained. Thus, the light-emitting element 300 is designed such that the excitation energy of the phosphorescent compound 311Bd emitting blue light is partly transferred to the phosphorescent compound 311Gd emitting green light and the excitation energy of the phosphorescent compound 311Gd emitting green light is partly transferred to the phosphorescent compound 311Rd emitting red light. Such energy transfer between isolated molecules becomes possible by utilizing dipole-dipole interaction (Förster mechanism).

As described above, the phosphorescent compounds are dispersed in the host materials and isolated from each other by the host materials; thus, there is no possibility that the whole excitation energy generated in the phosphorescent compound 311Bd emitting blue light is transferred to the phosphorescent compound 311Gd emitting green light and the phosphorescent compound 311Rd emitting red light by the Förster mechanism. For example, setting the thickness of the green light-emitting layer 311G in FIG. 2B to 20 nm or less allows energy to be partly transferred, so that all of the phosphorescent compound 311Bd, the phosphorescent compound 311Gd, and the phosphorescent compound 311Rd can be made to emit light.

Figure 3A:
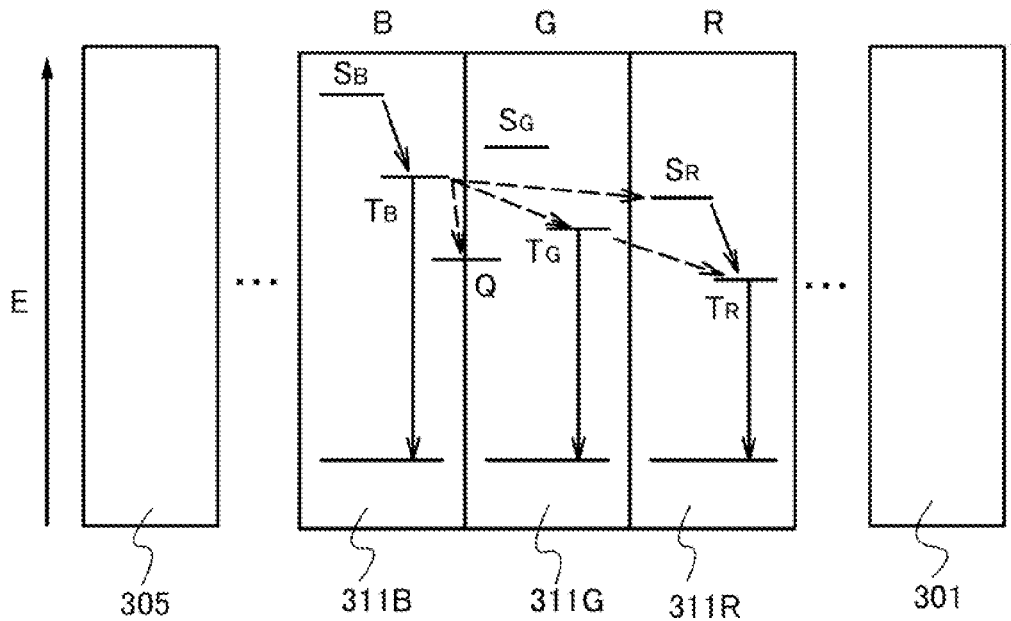
FIGS. 3A and 3B each illustrate energy transfer in light-emitting layers.

FIG. 3A schematically illustrates energy transfer between the phosphorescent compounds by the Förster mechanism in the light-emitting element 300. As illustrated in FIG. 3A, first, a singlet excited state formed in the phosphorescent compound 311Bd ($S_B$) is converted into a triplet excited state ($T_B$) by intersystem crossing. In other words, an exciton in the blue light-emitting layer 311B is basically brought into $T_B$.

Then, the energy of the exciton in $T_B$, some of which is converted into blue light emission, can be partly transferred to the triplet excited state of the phosphorescent compound 311Gd ($T_G$) by the Förster mechanism. This results from the fact that the phosphorescent compound 311Bd has a light-emitting property (has a high phosphorescence quantum yield φ) and that direct absorption, which corresponds to electron transition from a singlet ground state to a triplet excited state, is observed in the phosphorescent compound 311Gd (an absorption spectrum of a triplet excited state exists). When these conditions are fulfilled, triplet-triplet energy transfer from $T_B$ to $T_G$ by the Förster mechanism is possible. Further, energy transfer from $T_B$ to a singlet excited state of the phosphorescent compound 311Rd ($S_R$) can occur as long as the conditions for the Förster mechanism are fulfilled, although the contribution is slight. By intersystem crossing, $S_R$ is converted into a triplet excited state of the phosphorescent compound 311Rd ($T_R$) to contribute to emission by the phosphorescent compound 311Rd.

Note that a singlet excited state of the phosphorescent compound 311Gd ($S_G$) has higher energy than the triplet excited state of the phosphorescent compound 311Bd ($T_B$) in many cases and therefore does not contribute to the above energy transfer so much in many cases. For this reason, the description is omitted here.

Further, the energy of an exciton in $T_G$ of the phosphorescent compound 311Gd, some of which is converted into green light emission, can be partly transferred to the triplet excited state of the phosphorescent compound 311Rd ($T_R$) by the Förster mechanism. This results from the fact that the phosphorescent compound 311Gd has a light-emitting property (has a high phosphorescence quantum yield φ) and that direct absorption, which corresponds to electron transition from a singlet ground state to a triplet excited state, is observed in the phosphorescent compound 311Rd (an absorption spectrum of a triplet excited state exists). When these conditions are fulfilled, triplet-triplet energy transfer from $T_G$ to $T_R$ by the Förster mechanism is possible. The $T_R$ which results from such energy transfer is converted into red light emission of the phosphorescent compound 311Rd. In this manner, light emission can be obtained from each of the phosphorescent compounds.

Note that in the Förster mechanism, an energy donor (the phosphorescent compound 311Bd and the phosphorescent compound 311Gd in the light-emitting element 300) needs to have a light-emitting property; therefore, the phosphorescent compound 311Bd and the phosphorescent compound 311Gd each preferably have a phosphorescent quantum yield of 0.1 or more.

As described above, the comparative light-emitting element 300 has an element structure in which the phosphorescent compounds are isolated from each other with the use of the host materials and the stacked-layer structure and the phosphorescent compound that emits light with the shortest wavelength is mainly excited. Since energy is partly transferred by the Förster mechanism to a certain distance (e.g., 20 nm or less) in such an element structure, the excitation energy of the phosphorescent compound emitting blue light is partly transferred to the phosphorescent compound emitting green light, and further, the excitation energy of the phosphorescent compound emitting green light is partly transferred to the phosphorescent compound emitting red light. As a result, light emission can be obtained from each of the phosphorescent compounds.

However, if the blue light-emitting layer 311B deteriorates during driving, the energy of an exciton is partly quenched due to deteriorating substances. In other words, an energy level of a quencher is formed in a position denoted by Q in FIG. 3A. As illustrated in FIG. 3A, the energy of the quencher is probably lower than the energy of an exciton in $T_G$ of the phosphorescent compound 311Gd. Therefore, when the energy of the exciton in $T_B$ of the phosphorescent compound 311Bd is partly transferred to the quencher, the energy of an exciton on the quencher is hardly transferred to $T_G$ of the phosphorescent compound 311Gd and further, to $T_R$ of the phosphorescent compound 311Rd. That is, $T_G$ of the phosphorescent compound 311Gd, and further, $T_R$ of the phosphorescent compound 311Rd are prevented from being generated. This probably leads to reductions in lifetime and reliability of the light-emitting element 300.

<<Light-Emitting Element of One Embodiment of the Present Invention>>

In a light-emitting element of one embodiment of the present invention, three light-emitting layers are stacked such that one of the light-emitting layers that contains a phosphorescent compound emitting light of the shortest wavelength is adjacent to one of the light-emitting layers that contains a phosphorescent compound emitting light of the longest wavelength. Furthermore, in the light-emitting element of one embodiment of the present invention, carrier recombination occurs in each of the three light-emitting layers.

A light-emitting element of one embodiment of the present invention illustrated in FIG. 1A includes a first electrode 101, an EL layer 103 over the first electrode 101, and a second electrode 105 over the EL layer 103. One of the first electrode 101 and the second electrode 105 serves as an anode and the other serves as a cathode. In this embodiment, the first electrode 101 serves as an anode and the second electrode 105 serves as a cathode.

When a voltage higher than the threshold voltage of the light-emitting element is applied between the first electrode 101 and the second electrode 105, holes are injected from the first electrode 101 side to the EL layer 103 and electrons are injected from the second electrode 105 side to the EL layer 103. The injected electrons and holes are recombined in the EL layer 103 and a light-emitting substance contained in the EL layer 103 emits light.

The EL layer 103 includes at least a light-emitting layer 203. The EL layer 103 may further include, as a layer other than the light-emitting layer, a layer containing a hole-injection substance or an electron-injection substance, a hole-transport substance or an electron-transport substance, a bipolar substance (i.e., a substance in which the electron-transport property and the hole-transport property are high), or the like. Either a low molecular compound or a high molecular compound can be used for the EL layer 103, and an inorganic compound may also be contained.

As illustrated in FIG. 1A, the light-emitting element of one embodiment of the present invention includes, as the light-emitting layer 203, a first light-emitting layer 203x over the first electrode 101, a second light-emitting layer 203y over the first light-emitting layer 203x, and a third light-emitting layer 203z over the second light-emitting layer 203y. Here, unlike in a tandem structure, the first to third light-emitting layers are preferably provided in contact with each other. With this structure, distribution of carrier recombination regions in the light-emitting layers can be adjusted, which enables uniform light emission from the light-emitting layers for the respective colors.

The first light-emitting layer 203x contains a first phosphorescent compound and a first host material. The second light-emitting layer 203y contains a second phosphorescent compound and a second host material. The third light-emitting layer 203z contains a third phosphorescent compound and a third host material. Here, between a peak of an emission spectrum of the first phosphorescent compound, a peak of an emission spectrum of the second phosphorescent compound, and a peak of an emission spectrum of the third phosphorescent compound, the peak of the emission spectrum of the second phosphorescent compound is on the longest wavelength side, and the peak of the emission spectrum of the third phosphorescent compound is on the shortest wavelength side. The triplet excitation energy of the third host material is higher than that of the first host material and that of the second host material.

In the light-emitting element of one embodiment of the present invention, the first host material, the second host material, and the third host material each have an electron-transport property. Alternatively, in the light-emitting element of one embodiment of the present invention, the first host material, the second host material, and the third host material each have a hole-transport property. Further alternatively, in the light-emitting element of one embodiment of the present invention, the first host material, the second host material, and the third host material each have an electron-transport property and a hole-transport property. When any of these structures is applied to a light-emitting element, a carrier recombination region thereof widely spreads from the first light-emitting layer to the third light-emitting layer. Thus, the light-emitting substances contained in the light-emitting layers emit light with high efficiency, whereby a highly efficient multicolor light-emitting element can be provided.

When the third light-emitting layer (the light-emitting layer that contains the phosphorescent compound whose emission spectrum has a peak on the shortest wavelength side) is provided on the anode side, for example, the host materials of the light-emitting layers preferably have a hole-transport property. Further, when the third light-emitting layer is provided on the cathode side as in this embodiment, the host materials of the light-emitting layers preferably have an electron-transport property.

In addition, it is preferable that the first host material, the second host material, and the third host material each have a hole-transport skeleton and an electron-transport skeleton.

Examples of a hole-transport skeleton include an aromatic amine and a π-electron rich heteroaromatic ring. A π-electron rich heteroaromatic ring is particularly preferable because it has high chemical and thermal stabilities. Examples of a π-electron rich heteroaromatic ring include a heteroaromatic ring having a pyrrole skeleton, a heteroaromatic ring having a furan skeleton, and a heteroaromatic ring having a thiophene skeleton. As specific examples, a carbazole skeleton, a dibenzo[c,g]carbazole skeleton, a dibenzofuran skeleton, and a dibenzothiophene skeleton can be given.

A preferable example of an electron-transport skeleton is a π-electron deficient heteroaromatic ring because it has an excellent electron-transport property. Examples of a π-electron deficient heteroaromatic ring include a heteroaromatic ring having a pyridine skeleton, a heteroaromatic ring having a phthalazine skeleton, a heteroaromatic ring having a pyrimidine skeleton, a heteroaromatic ring having a pyrazine skeleton, a heteroaromatic ring having a triazine skeleton, a heteroaromatic ring having an imidazole skeleton, a heteroaromatic ring having an oxazole skeleton, a heteroaromatic ring having a thiazole skeleton, and a heteroaromatic ring having a triazole skeleton. As specific examples, a pyridine skeleton, a pyrimidine skeleton, a quinoxaline skeleton, a dibenzo[f,h]quinoxaline skeleton, and a benzimidazole skeleton can be given.

The host materials may have different hole-transport skeletons and electron-transport skeletons or the same hole-transport skeleton and electron-transport skeleton.

Note that because the triplet excitation energy of the third host material is higher than that of the first host material and that of the second host material, the hole-transport skeleton and the electron-transport skeleton of the third host material are preferably different from the hole-transport skeleton and the electron-transport skeleton of each of the first host material and the second host material. Further, the electron-transport skeleton of the third host material preferably has triplet excitation energy higher than that of the electron-transport skeleton of each of the first host material and the second host material.

It is preferable that the first host material and the second host material have the same hole-transport skeleton and electron-transport skeleton, and it is particularly preferable that the first host material and the second host material have the same electron-transport skeleton. This is because carriers need to be transferred smoothly between the first light-emitting layer and the second light-emitting layer in order that carrier recombination can occur in each of the first light-emitting layer and the second light-emitting layer. Accordingly, the first host material is preferably the same as the second host material.

In the light-emitting element of one embodiment of the present invention, the first light-emitting layer may contain a first carrier-transport compound. In that case, one of the first host material and the first carrier-transport compound is a hole-transport compound and the other is an electron-transport compound. It is particularly preferable that a combination of the first host material and the first carrier-transport compound forms an exciplex.

Similarly, in the light-emitting element of one embodiment of the present invention, the second light-emitting layer may contain a second carrier-transport compound. In that case, one of the second host material and the second carrier-transport compound is a hole-transport compound and the other is an electron-transport compound. It is particularly preferable that a combination of the second host material and the second carrier-transport compound forms an exciplex.

Similarly, in the light-emitting element of one embodiment of the present invention, the third light-emitting layer may contain a third carrier-transport compound. In that case, one of the third host material and the third carrier-transport compound is a hole-transport compound and the other is an electron-transport compound. It is particularly preferable that a combination of the third host material and the third carrier-transport compound forms an exciplex.

The transport property of the light-emitting layer containing the carrier-transport compound can be adjusted by changing the mixture ratio between the host material and the carrier-transport compound (i.e., the electron-transport compound and the hole-transport compound).

A more specific example of the light-emitting layer 203 is illustrated in FIG. 1B. The light-emitting layer 203 illustrated in FIG. 1B includes, from the first electrode 101 side, a green light-emitting layer 203G containing a phosphorescent compound 203Gd emitting green light and a host material 203Gh; a red light-emitting layer 203R containing a phosphorescent compound 203Rd emitting red light and a host material 203Rh; and a blue light-emitting layer 203B containing a phosphorescent compound 203Bd emitting blue light and a host material 203Bh. The phosphorescent compounds contained in the light-emitting layers are dispersed in the respective host materials and isolated from each other by the host materials.

In that case, between the phosphorescent compounds, energy transfer by electron exchange interaction (what is called Dexter mechanism) is suppressed. In other words, the excitation energy of the phosphorescent compound 203Bd emitting blue light is not easily transferred by the Dexter mechanism to the phosphorescent compound 203Gd emitting green light or the phosphorescent compound 203Rd emitting red light. Furthermore, the excitation energy of the phosphorescent compound 203Gd emitting green light is not easily transferred by the Dexter mechanism to the phosphorescent compound 203Rd emitting red light. Thus, a phenomenon in which the phosphorescent compound 203Rd emitting light of the longest wavelength mainly emits light is suppressed.

In the light-emitting element which includes the structure of the light-emitting layer 203 illustrated in FIG. 1B, a carrier recombination region widely spreads from the blue light-emitting layer 203B to the green light-emitting layer 203G. That is, the carrier recombination region exists in the blue light-emitting layer 203B, the red light-emitting layer 203R, and the green light-emitting layer 203G.

In the light-emitting element of one embodiment of the present invention, carrier recombination occurs in each of the layers included in the light-emitting layer 203. Here, a singlet excited state ($S_B$) generated in the phosphorescent compound 203Bd emitting blue light is converted into a triplet excited state ($T_B$) by intersystem crossing. In other words, an exciton in the blue light-emitting layer 203B is basically brought into $T_B$. The energy of the exciton in $T_B$ is converted into blue light emission. Similarly, a singlet excited state ($S_R$) generated in the phosphorescent compound 203Rd emitting red light is converted into a triplet excited state ($T_R$) by intersystem crossing. In other words, an exciton in the red light-emitting layer 203R is basically brought into $T_R$. The energy of the exciton in $T_R$ is converted into red light emission. Similarly, a singlet excited state ($S_G$) generated in the phosphorescent compound 203Gd emitting green light is converted into a triplet excited state ($T_G$) by intersystem crossing. In other words, an exciton in the green light-emitting layer 203G is basically brought into $T_G$. The energy of the exciton in $T_G$ is converted into green light emission.

When a carrier recombination region is included in each of the light-emitting layers in the light-emitting element as described above, carrier recombination occurs in each of the light-emitting layers, which makes it possible to obtain light emission from each of the phosphorescent compounds in the light-emitting layers.

Here, the light-emitting element of one embodiment of the present invention is designed such that the energy of an exciton in $T_B$ is partly transferred to the phosphorescent compound 203Rd and the phosphorescent compound 203Gd. Such energy transfer between isolated molecules becomes possible by utilizing dipole-dipole interaction (Förster mechanism).

As described above, the phosphorescent compounds are dispersed in the host materials and isolated from each other by the host materials; thus, there is no possibility that the whole excitation energy generated in the phosphorescent compound 203Bd is transferred to the phosphorescent compound 203Rd and the phosphorescent compound 203Gd by the Förster mechanism. For example, setting the thickness of the red light-emitting layer 203R in FIG. 1B to greater than or equal to 2 nm and less than or equal to 20 nm allows energy to be partly transferred, so that the phosphorescent compound 203Bd, the phosphorescent compound 203Rd, and the phosphorescent compound 203Gd can be made to emit light.

Figure 3B:
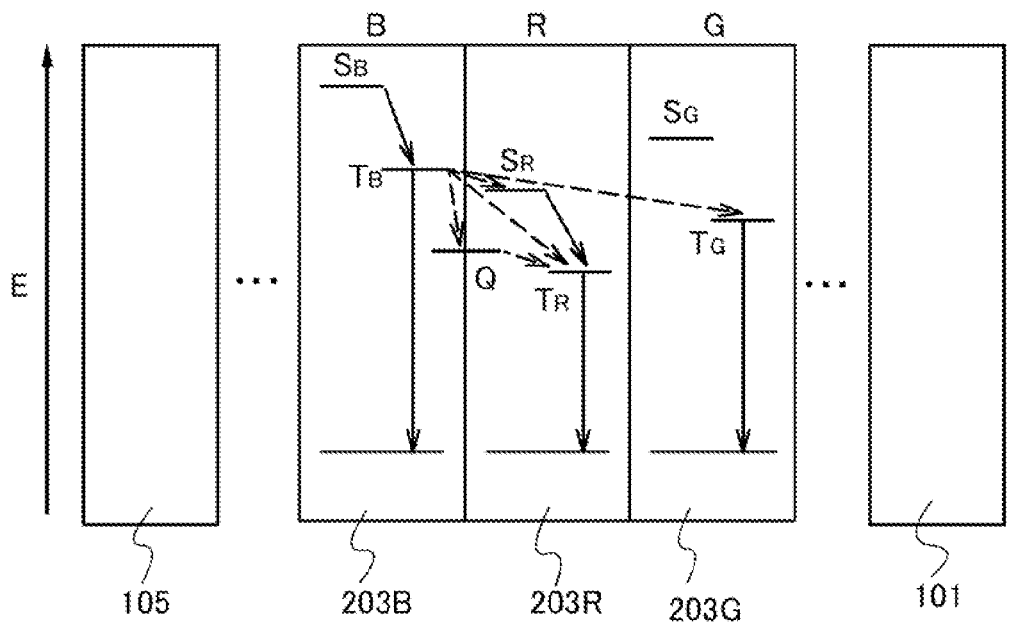

FIG. 3B schematically illustrates energy transfer between the phosphorescent compounds by the Förster mechanism in the light-emitting element of one embodiment of the present invention. As illustrated in FIG. 3B, first, a singlet excited state formed in the phosphorescent compound 203Bd ($S_B$) is converted into a triplet excited state ($T_B$) by intersystem crossing. In other words, an exciton in the blue light-emitting layer 203B is basically brought into $T_B$.

Then, the energy of the exciton in $T_B$, some of which is converted into blue light emission, can be partly transferred to the triplet excited state of the phosphorescent compound 203Gd ($T_G$) by the Förster mechanism. This results from the fact that the phosphorescent compound 203Bd has a light-emitting property (has a high phosphorescence quantum yield ϕ) and that direct absorption, which corresponds to electron transition from a singlet ground state to a triplet excited state, is observed in the phosphorescent compound 203Gd (an absorption spectrum of a triplet excited state exists). When these conditions are fulfilled, triplet-triplet energy transfer from $T_B$ to $T_G$ by the Förster mechanism is possible. Further, energy transfer from $T_B$ to a triplet excited state of the phosphorescent compound 203Gd ($T_G$) can occur as long as the conditions for the Förster mechanism are fulfilled, although the contribution is slight. $T_G$ contributes to light emission by the phosphorescent compound 203Gd. Note that since the energy donor in the Förster mechanism (here, the phosphorescent compound 203Bd) needs to have a light-emitting property, the phosphorescence quantum yield of the phosphorescent compound 203Bd is preferably 0.1 or more.

Also in the light-emitting element of one embodiment of the present invention, if the blue light-emitting layer 203B deteriorates during driving, the energy of an exciton is partly quenched due to deteriorating substances. In other words, an energy level of a quencher is formed in a position denoted by Q in FIG. 3B. However, the energy of the quencher is probably higher than the energy of an exciton in $T_R$ of the phosphorescent compound 311Rd as illustrated in FIG. 3B; thus, when the energy of the exciton in $T_B$ of the phosphorescent compound 311Bd is partly transferred to the quencher, the energy of an exciton on the quencher can be transferred to $T_R$ of the phosphorescent compound 311Rd. Therefore, as compared to the comparative light-emitting element 300, in the light-emitting element of one embodiment of the present invention, formation of $T_G$ of the phosphorescent compound 311Gd and $T_R$ of the phosphorescent compound 311Rd is less likely to be inhibited by the quencher. Accordingly, by application of one embodiment of the present invention, a light-emitting element having a longer lifetime and higher reliability than the comparative light-emitting element 300 can be provided.

In other words, when the light-emitting layer adjacent to the light-emitting layer in which a quencher is generated contains the phosphorescent compound whose triplet excitation energy is lower than the energy of the quencher, it is possible to prevent reductions in lifetime and reliability of the light-emitting element due to generation of a quencher.

Note that the host material 203Rh is preferably the same as the host material 203Gh, in which case carriers easily reach the green light-emitting layer 203G and energy is easily transferred from $T_B$ to $T_G$.

As described above, in the light-emitting element of one embodiment of the present invention, carrier recombination occurs in each of the light-emitting layers and accordingly, light emission can be obtained from each of the phosphorescent compounds contained in the light-emitting layers. Further, in energy transfer between the light-emitting layers by the Förster mechanism, formation of a triplet excited state is not prevented by a quencher. Thus, a light-emitting element in which a plurality of light-emitting substances emit light in a good balance can be provided. In addition, a light-emitting element having high emission efficiency can be provided. Further, a highly reliable light-emitting element can be provided.

Another example of the light-emitting element of one embodiment of the present invention will be described below.

A light-emitting element shown in FIG. 1C includes a hole-injection layer 201 over the first electrode 101 and a hole-transport layer 202 over the hole-injection layer 201, which are provided between the first electrode 101 and the first light-emitting layer 203x. Further, an electron-transport layer 204 over the third light-emitting layer 203z and an electron-injection layer 205 over the electron-transport layer 204 are provided between the third light-emitting layer 203z and the second electrode 105. Note that the first light-emitting layer 203x, the second light-emitting layer 203y, and the third light-emitting layer 203z may have the same structures as those in FIG. 1B.

A light-emitting element shown in FIG. 1D includes the first electrode 101, the EL layer 103 over the first electrode 101, a charge-generation region 107 over the EL layer 103, and the second electrode 105 over the charge-generation region 107. The EL layer 103 has the same structure as that in FIG. 1A.

As in a light-emitting element illustrated in FIG. 1E, a plurality of EL layers may be stacked between the first electrode 101 and the second electrode 105. In this case, a charge-generation region 107 is preferably provided between the stacked EL layers.

The light-emitting element shown in FIG. 1E includes the first electrode 101, an EL layer 103a over the first electrode 101, the charge-generation region 107 over the EL layer 103a, an EL layer 103b over the charge-generation region 107, and the second electrode 105 over the EL layer 103b. At least one of the EL layers 103a and 103b has the same structure as that in FIG. 1A.

Behavior of electrons and holes in the charge-generation region 107 provided between the EL layer 103a and the EL layer 103b is described. When a voltage higher than the threshold voltage of the light-emitting element is applied between the first electrode 101 and the second electrode 105, holes and electrons are generated in the charge-generation region 107, and the holes move into the EL layer 103b provided on the second electrode 105 side and the electrons move into the EL layer 103a provided on the first electrode 101 side. The holes injected into the EL layer 103b are recombined with the electrons injected from the second electrode 105 side, so that a light-emitting substance contained in the EL layer 103b emits light. Further, the electrons injected into the EL layer 103a are recombined with the holes injected from the first electrode 101 side, so that a light-emitting substance contained in the EL layer 103a emits light. Thus, the holes and electrons generated in the charge-generation region 107 cause light emissions in different EL layers.

Note that the EL layers can be provided in contact with each other with no charge-generation region 107 provided therebetween when these EL layers allow the same structure as the charge-generation region 107 to be formed therebetween. For example, when the charge-generation region is formed over one surface of an EL layer, another EL layer can be provided in contact with the surface.

The structures of the layers provided between the first electrode 101 and the second electrode 105 are not limited to the above-described structures. Preferably, a light-emitting region where holes and electrons recombine is positioned away from the first electrode 101 and the second electrode 105 so that quenching due to the proximity of the light-emitting region and a metal used for the electrodes and carrier-injection layers can be prevented.

Further, in order that transfer of energy from an exciton generated in the light-emitting layer can be suppressed, preferably, the hole-transport layer and the electron-transport layer which are in contact with the light-emitting layer 203 are formed using a substance having higher triplet excitation energy than the substance in the light-emitting layer.

<<Materials of Light-Emitting Element>>

Examples of materials that can be used for each layer will be described below. Note that each layer other than the light-emitting layer may have a single-layer structure or a stacked-layer structure including two or more layers.

<Anode>

The electrode serving as the anode can be formed using one or more kinds of conductive metals and alloys, conductive compounds, and the like. In particular, it is preferable to use a material with a high work function (4.0 eV or more). Examples include indium tin oxide (ITO), indium tin oxide containing silicon or silicon oxide, indium zinc oxide, indium oxide containing tungsten oxide and zinc oxide, graphene, gold, platinum, nickel, tungsten, chromium, molybdenum, iron, cobalt, copper, palladium, titanium, and a nitride of a metal material (e.g., titanium nitride). Alternatively, the electrode may be formed as follows: silver, copper, aluminum, titanium, or the like is formed to have a nanowire shape (or a stripe shape or a thin-stripe shape), and then a conductive substance (a conductive organic material, graphene, or the like) is formed thereover by a coating method, a printing method, or the like.

When the anode is in contact with the charge-generation region, any of a variety of conductive materials can be used regardless of their work functions; for example, aluminum, silver, an alloy containing aluminum, or the like can be used.

<Cathode>

The electrode serving as the cathode can be formed using one or more kinds of conductive metals and alloys, conductive compounds, and the like. In particular, it is preferable to use a material with a low work function (3.8 eV or less). Examples include aluminum, silver, an element belonging to Group 1 or 2 of the periodic table (e.g., an alkali metal such as lithium or cesium, an alkaline earth metal such as calcium or strontium, or magnesium), an alloy containing any of these elements (e.g., Mg—Ag or Al—Li), a rare earth metal such as europium or ytterbium, and an alloy containing any of these rare earth metals.

Note that in the case where the cathode is in contact with the charge-generation region, a variety of conductive materials can be used regardless of its work function. For example, ITO or indium tin oxide containing silicon or silicon oxide can be used.

The electrodes each can be formed by a vacuum evaporation method or a sputtering method. Alternatively, when a silver paste or the like is used, a coating method or an inkjet method can be used.

Emitted light is extracted out through one or both of the first electrode 101 and the second electrode 105. Therefore, one or both of the first electrode 101 and the second electrode 105 are light-transmitting electrodes. In the case where only the first electrode 101 is a light-transmitting electrode, light is extracted through the first electrode 101. In the case where only the second electrode 105 is a light-transmitting electrode, light emission is extracted through the second electrode 105. In the case where both the first electrode 101 and the second electrode 105 are light-transmitting electrodes, light emission is extracted through the first electrode 101 and the second electrode 105. A material that reflects light is preferably used as the electrode through which light is not extracted.

In addition, an insulating film such as an organic film, a transparent semiconductor film, or a silicon nitride film may be formed over the cathode (or an upper electrode). These films serve as passivation films and can suppress entry of impurities and moisture into the light-emitting element, or can reduce loss of light energy due to surface plasmon in the cathode.

<Light-Emitting Layer>

As already described above, the light-emitting element in this embodiment includes three kinds of light-emitting layers, each of which contains a phosphorescent compound and a host material.

The phosphorescent compound can be referred to as a guest material in each of the light-emitting layers. A compound in which the phosphorescent compound is dispersed can be referred to as a host material. Each of the light-emitting layers may further contain a material other than the guest material and the host material. In the present specification, a compound accounting for the largest proportion of the light-emitting layer is a host material in the light-emitting layer.

When the light-emitting layer has the structure in which the guest material is dispersed in the host material, the crystallization of the light-emitting layer can be inhibited. Further, concentration quenching due to high concentration of the guest material can be suppressed and thus the light-emitting element can have high emission efficiency. An electron-transport compound and a hole-transport compound which will be described below can be used as the host materials.

Note that the $T_1$ level (the level of triplet excitation energy) of the host material (or a material other than the guest material in the light-emitting layer) is preferably higher than the $T_1$ level of the guest material. This is because, when the $T_1$ level of the host material is lower than that of the guest material, the triplet excitation energy of the guest material, which is to contribute to light emission, is quenched by the host material and accordingly the emission efficiency is decreased.

As examples of a phosphorescent compound emitting blue light, compounds having an emission peak at 440 nm to 520 nm can be given. The following are the specific examples: an organometallic iridium complex having a 4H-triazole skeleton, such as tris{2-[5-(2-methylphenyl)-4-(2,6-dimethylphenyl)-4H-1,2,4-triazol-3-yl-κN2]phenyl-κC}iridium(III) (abbreviation: [Ir(mpptz-dmp)$_3$]), tris(5-methyl-3,4-diphenyl-4H-1,2,4-triazolato)iridium(III) (abbreviation: Ir(Mptz)$_3$), or tris[4-(3-biphenyl)-5-isopropyl-3-phenyl-4H-1,2,4-triazolato]iridium(III) (abbreviation: Ir(iPrptz-3b)$_3$): an organometallic iridium complex having a 1H-triazole skeleton, such as tris[3-methyl-1-(2-methylphenyl)-5-phenyl-1H-1,2,4-triazolato]iridium(III) (abbreviation: Ir(Mptz1-mp)$_3$) or tris(1-methyl-5-phenyl-3-propyl-1H-1,2,4-triazolato)iridium(III) (abbreviation: Ir(PrptzI-Me)$_3$); an organometallic iridium complex having an imidazole skeleton, such as fac-tris[1-(2,6-diisopropylphenyl)-2-phenyl-1H-imidazole]iridium(III) (abbreviation: Ir(iPrpmi)$_3$) or tris[3-(2,6-dimethylphenyl)-7-methylimidazo[1,2-f]phenanthridinato]iridium(III) (abbreviation: Ir(dmpimpt-Me)$_3$); and an organometallic iridium complex in which a phenylpyridine derivative having an electron-withdrawing group is a ligand, such as bis[2-(4',6'-difluorophenyl)pyridinato-N,C$^{2'}$]iridium(III) tetrakis(l-pyrazolyl)borate (abbreviation: FIr6), bis[2-(4',6'-difluorophenyl)pyridinato-N,C$^{2'}$]iridium(III) picolinate (abbreviation: FIrpic), bis{2-[3',5'-bis(trifluoromethyl)phenyl]pyridinato-N,C$^{2'}$})iridium(III) picolinate (abbreviation: Ir(CF$_3$ppy)$_2$(pic)), or bis[2-(4',6'-difluorophenyl)pyridinato-N,C$^{2'}$]iridium(III) acetylacetonate (abbreviation: FIracac).

Among the materials given above, the organometallic iridium complex having a 4H-triazole skeleton has high reliability and high emission efficiency and is thus especially preferable.

An organometallic iridium complex having a polyazole skeleton such as a 4H-triazole skeleton, a 1H-triazole skeleton, or an imidazole skeleton has a high hole-trapping property. Thus, it is preferable that such a compound be used as a phosphorescent compound emitting blue light in the light-emitting element of one embodiment of the present invention and the blue light-emitting layer be closer to the cathode than the red light-emitting layer and the green light-emitting layer are, because in that case, a reduction (or a reduction over time) in emission efficiency due to holes penetrating the blue light-emitting layer can be prevented.

As examples of a phosphorescent compound emitting green light, compounds having an emission peak at 520 nm to 600 nm can be given. The following are the specific examples: an organometallic iridium complex having a pyrimidine skeleton, such as tris(4-methyl-6-phenylpyrimidinato)iridium(III) (abbreviation: [Ir(mppm)$_3$]), tris(4-t-butyl-6-phenylpyrimidinato)iridium(III) (abbreviation: [Ir(tBuppm)$_3$]), (acetylacetonato)bis(6-methyl-4-phenylpyrimidinato)iridium(III) (abbreviation: [Ir(mppm)$_2$(acac)]), (acetylacetonato)bis(6-ter-butyl-4-phenylpyrimidinato)iridium(III) (abbreviation: [Ir(tBuppm)$_2$(acac)]), (acetylacetonato)bis(4-(2-norbornyl)-6-phenylpyrimidinato iridium(III) (endo-and exo-mixture) (abbreviation: [Ir(nbppm)$_2$(acac)]), (acetylacetonato)bis[5-methyl-6-(2-methylphenyl)-4-phenylpyrimidinatol]iridium(III) (abbreviation: [Ir(mpmppm)$_2$(acac)]), or (acetylacetonato)bis(4,6-diphenylpyrimidinato)iridium(III) (abbreviation: [Ir(dppm)$_2$(acac)]): an organometallic iridium complex having a pyrazine skeleton, such as (acetylacetonato)bis(3,5-dimethyl-2-phenylpyrazinato)iridium(III) (abbreviation: [Ir(mppr-Me)$_2$(acac)]) or (acetylacetonato)bis (5-isopropyl-3-methyl-2-phenylpyrazinato)iridium(III) (abbreviation: [Ir(mppr-iPr)$_2$(acac)]); an organometallic iridium complex having a pyridine skeleton, such as tris(2-phenylpyridinato-N,C$^{2'}$)iridium(III) (abbreviation: [Ir(ppy)$_3$]), bis(2-phenylpyridinato-N,C$^{2'}$)iridium(III) acetylacetonate (abbreviation: [Ir(ppy)$_2$(acac)]), bis(benzo[h]quinolinato)iridium (III) acetylacetonate (abbreviation: [Ir(bzq)$_2$(acac)]), tris (benzo[h]quinolinato)iridium(III) (abbreviation: [Ir(bzq)$_3$]), tris(2-phenylquinolinato-N,C$^{2'}$)iridium(III) (abbreviation: [Ir(pq)$_3$]), or bis(2-phenylquinolinato-N,C$^{2'}$)iridium(III) acetylacetonate (abbreviation: [Ir(pq)$_2$(acac)]); and a rare earth metal complex such as tris(acetylacetonato) (monophenanthroline)terbium(III) (abbreviation: [Tb(acac)$_3$ (Phen)]).

Among the materials given above, the organometallic iridium complex having a pyrimidine skeleton has distinctively high reliability and distinctively high emission efficiency and is thus especially preferable.

Furthermore, among the above materials, an organometallic iridium complex having a diazine skeleton such as a pyrimidine skeleton or a pyrazine skeleton has a low hole-trapping property and a high electron-trapping property. Thus, it is preferable that such a compound be used as a phosphorescent compound emitting green light in the light-emitting element of one embodiment of the present invention and the green light-emitting layer be closer to the anode than the red light-emitting layer and the blue light-emitting layer are, because in that case, holes are easily transported to the red light-emitting layer and the blue light-emitting layer and a reduction (or a reduction over time) in emission efficiency due to electrons penetrating the green light-emitting layer can be prevented.

As examples of a phosphorescent compound emitting red light, compounds having an emission peak at 600 nm to 750 nm can be given. The following are the specific examples: an organometallic iridium complex having a pyrimidine skeleton, such as (diisobutyrylmethanato)bis[4,6-bis(3-methylphenyl)pyrimidinato]iridium(III) (abbreviation: [Ir(5mdppm)$_2$(dibm)]), bis[4,6-bis(3-methylphenyl)pyrimidinato] (dipivaloylmethanato)iridium(III) (abbreviation: [Ir (5mdppm)$_2$(dpm)]), or bis[4,6-di(naphthalen-1-yl) pyrimidinato](dipivaloylmethanato)iridium(III) (abbreviation: [Ir(d1npm)$_2$(dpm)]); an organometallic iridium complex having a pyrazine skeleton, such as (acetylacetonato)bis(2,3,5-triphenylpyrazinato)iridium(III) (abbreviation: [Ir(tppr)$_2$(acac)]), bis(2,3,5-triphenylpyrazinato) (dipivaloylmethanato)iridium(III) (abbreviation: [Ir(tppr)$_2$ (dpm)]), or (acetylacetonato)bis[2,3-bis(4-fluorophenyl) quinoxalinato]iridium(II) (abbreviation: [Ir(Fdpq)$_2$acac]): an organometallic iridium complex having a pyridine skeleton, such as tris(1-phenylisoquinolinato-N,C$^{2'}$)iridium(III) (abbreviation: [Ir(piq)$_3$]) or bis(1-phenylisoquinolinato-N,C$^{2'}$) iridium(III) acetylacetonate (abbreviation: [Ir(piq)$_2$acac]); a platinum complex such as 2,3,7,8,12,13,17,18-octaethyl-21H,23H-porphyrin platinum(II) (abbreviation: PtOEP): and a rare earth metal complex such as tris(1,3-diphenyl-1,3-propanedionato)(monophenanthroline)europium(III) (abbreviation: [Eu(DBM)$_3$(Phen)]) or tris[1-(2-thenoyl)-3,3,3-trifluoroacetonato](monophenanthroline)europium(III) (abbreviation: [Eu(TTA)$_3$(Phen)]).

Among the materials given above, the organometallic iridium complex having a pyrimidine skeleton has distinctively high reliability and distinctively high emission efficiency and is thus especially preferable. Further, because an organometallic iridium complex having a pyrazine skeleton can provide red light emission with favorable chromaticity, the use of the organometallic iridium complex in a white light-emitting element improves a color rendering property of the white light-emitting element.

Furthermore, among the above materials, an organometallic iridium complex having a diazine skeleton such as a pyrimidine skeleton or a pyrazine skeleton has a low hole-trapping property and a high electron-trapping property. Thus, it is preferable that an organometallic iridium complex having a diazine skeleton be used as a phosphorescent compound emitting red light and the red light-emitting layer be closer to the anode than the blue light-emitting layer is, because in that case, holes are easily transported to the blue light-emitting layer and a reduction (or a reduction over time) in emission efficiency due to electrons penetrating the red light-emitting layer can be prevented.

Note that the phosphorescent compound may be replaced with a material exhibiting thermally activated delayed fluorescence. i.e., a thermally activated delayed fluorescence (TADF) material. Here, the term "delayed fluorescence" refers to light emission having a spectrum similar to that of normal fluorescence and an extremely long lifetime. The lifetime is $10^{-6}$ seconds or longer, preferably $10^{-3}$ seconds or longer. Specific examples of the thermally activated delayed fluorescence materials include a fullerene, a derivative thereof, an acridine derivative such as proflavine, and eosin. Besides, a metal-containing porphyrin can be used, such as a porphyrin containing magnesium (Mg), zinc (Zn), cadmium (Cd), tin (Sn), platinum (Pt), indium (In), or palladium (Pd). Examples of the metal-containing porphyrin include a protoporphyrin-tin fluoride complex (abbreviation: SnF$_2$(Proto IX)), a mesoporphyrin-tin fluoride complex (abbreviation: SnF$_2$(Meso IX)), a hematoporphyrin-tin fluoride complex (abbreviation: SnF$_2$(Hemato IX)), a coproporphyrin tetramethyl ester-tin fluoride complex (abbreviation: SnF$_2$(Copro III-4Me)), an octaethylporphyrin-tin fluoride complex (abbreviation: SnF$_z$(OEP)), an etioporphyrin-tin fluoride complex (abbreviation: SnF$_2$(Etio 1)), and an octaethylporphyrin-platinum chloride complex (abbreviation: PtCl$_2$(OEP)). Alternatively, a heterocyclic compound including a π-electron rich heteroaromatic ring and a π-electron deficient heteroaromatic ring can be used, such as 2-(biphenyl-4-yl)-4,6-bis(12-phenylindolo[2,3-a]carbazol-11-yl)-1,3,5-triazine (abbreviation: PIC-TRZ). Note that a substance in which a π-electron rich heteroaromatic ring is directly bonded to a π-electron deficient heteroaromatic ring is particularly preferably used because the donor property of the π-electron rich heteroaromatic ring and the acceptor property of the π-electron deficient heteroaromatic ring are both increased and the difference between the S$_1$ level (the level of singlet excitation energy) and the T$_1$ level becomes small.

As the electron-transport compound, a π-electron deficient heteroaromatic compound such as a nitrogen-containing heteroaromatic compound, a metal complex having a quinoline skeleton or a benzoquinoline skeleton, a metal complex having an oxazole-based or thiazole-based ligand, or the like can be used.

Specific examples include the following: metal complexes such as bis(10-hydroxybenzo[h]quinolinato)beryllium (abbreviation: BeBq$_2$), bis(2-methyl-8-quinolinolato) (4-phenylphenolato)aluminum (abbreviation: BAlq), bis(8-quinolinolato)zinc(II) (abbreviation: Znq), bis[2-(2-hydroxyphenyl) benzoxazolato]zinc (abbreviation: Zn(BOX)$_2$), and bis[2-(2-hydroxyphenyl)benzothiazolato]zinc (abbreviation: Zn(BTZ)$_2$); heterocyclic compounds having polyazole skeletons, such as 2-(4-biphenylyl)-5-(4-tert-butylphenyl)-1,3,4-oxadiazole (abbreviation: PBD), 3-(4-biphenylyl)-4-phenyl- 5-(4-tert-butylphenyl)-1,2,4-triazole (abbreviation: TAZ), 1,3-bis[5-(p-teri-butylphenyl)-1,3,4-oxadiazol-2-yl]benzene (abbreviation: OXD-7), 9-[4-(5-phenyl-1,3,4-oxadiazol-2-yl)phenyl]-9H-carbazole (abbreviation: COII), 2,2',2"-(1,3,5-benzenetriyl)tris(1-phenyl-1H-benzimidazole) (abbreviation: TPBI), and 2-[3-(dibenzothiophen-4-yl)phenyl]-1-phenyl-1H-benzimidazole (abbreviation: mDBTBIm-II); heterocyclic compounds having quinoxaline skeletons or dibenzoquinoxaline skeletons, such as 2-[3-(dibenzothiophen-4-yl)phenyl]dibenzo[f,h]quinoxaline (abbreviation: 2mDBTPDBq-II), 2-[3'-(dibenzothiophen-4-yl)biphenyl-3-yl]dibenzo[f,h]quinoxaline (abbreviation: 2mDBTBPDBq-II), 2-[4-(3,6-diphenyl-9H-carbazol-9-yl)phenyl]dibenzo[f,h]quinoxaline (abbreviation: 2CzPDBq-III), 7-[3-(dibenzothiophen-4-yl)phenyl]dibenzo[f,h]quinoxaline (abbreviation: 7mDBTPDBq-II), 6-[3-(dibenzothiophen-4-yl)phenyl]dibenzo[f,h]quinoxaline (abbreviation: 6mDBTPDBq-II), and 2-[3'-(9H-carbazol-9-yl)biphenyl-3-yl]dibenzo[f,h]quinoxaline (abbreviation: 2mCzBPDBq); heterocyclic compounds having diazine skeletons (pyrimidine skeletons or pyrazine skeletons), such as 4,6-bis[3-(phenanthren-9-yl)phenyl]pyrimidine (abbreviation: 4,6mPnP2Pm), 4,6-bis[3-(9H-carbazol-9-yl)phenyl]pyrimidine (abbreviation: 4,6mCzP2Pm), and 4,6-bis[3-(4-dibenzothienyl)phenyl]pyrimidine (abbreviation: 4,6mDBTP2Pm-II); heterocyclic compounds having pyridine skeletons, such as 3,5-bis[3-(9H-carbazol-9-yl)phenyl]pyridine (abbreviation: 3,5DCzPPy), 1,3,5-tri[3-(3-pyridyl)phenyl]benzene (abbreviation: TmPyPB), and 3,3',5,5'-tetra[(m-pyridyl)-phen-3-yl]biphenyl (abbreviation: BP4mPy). Among the above-described compounds, the heterocyclic compounds having quinoxaline skeletons or dibenzoquinoxaline skeletons, the heterocyclic compounds having diazine (pyrimidine or pyrazine) skeletons, and the heterocyclic compounds having pyridine skeletons have favorable reliability and can be preferably used. Specifically, a heterocyclic compound having a diazine skeleton has a high electron-transport property to contribute to a reduction in drive voltage.

The following examples can also be given: metal complexes having quinoline skeletons or benzoquinoline skeletons, such as tris(8-quinolinolato)aluminum (abbreviation: Alq) and tris(4-methyl-8-quinolinolato)aluminum (abbreviation: Almq$_3$); and heteroaromatic compounds such as bathophenanthroline (abbreviation: BPhen), bathocuproine (abbreviation: BCP), 3-(4-tert-butylphenyl)-4-(4-ethylphenyl)-5-(4-biphenylyl)-1,2,4-triazole (abbreviation: p-EtTAZ), and 4,4'-bis(5-methylbenzoxazol-2-yl)stilbene (abbreviation: BzOs). In addition, high molecular compounds such as poly(2,5-pyridinediyl) (abbreviation: PPy), poly[(9,9-dihexylfluorene-2,7-diyl)-co-(pyridine-3,5-diyl)] (abbreviation: PF-Py), and poly[(9,9-dioctylfluorene-2,7-diyl)-co-(2,2'-bipyridine-6,6'-diyl)] (abbreviation: PF-BPy) can also be given.

Further, an electron-transport compound which easily accepts holes such as 9-[4-(10-phenyl-9-anthracenyl)phenyl]-9H-carbazole (abbreviation: CzPA), 9-phenyl-3-[4-(10-phenyl-9-anthryl)phenyl]-9H-carbazole (abbreviation: PCzPA), 3,6-diphenyl-9-[4-(10-phenyl-9-anthryl)phenyl]-9H-carbazole (abbreviation: DPCzPA), 9,10-bis(3,5-diphenylphenyl)anthracene (abbreviation: DPPA), 9,10-di(2-naphthyl)anthracene (abbreviation: DNA), or 2-tert-butyl-9,10-di(2-naphthyl)anthracene (abbreviation: t-BuDNA) can be preferably used. In the light-emitting element of one embodiment of the present invention, the electron-transport compound that disperses the blue-light-emitting hole-trapping fluorescent compound preferably has an anthracene skeleton to have a hole-trapping property in addition to an electron-transport property.

As the hole-transport compound, a compound having an aromatic amine skeleton, a compound having a carbazole skeleton, a compound having a thiophene skeleton, a compound having a furan skeleton, or the like can be used. In particular, a n-electron rich heteroaromatic compound is preferable. A compound having an aromatic amine skeleton and a compound having a carbazole skeleton are preferable because these compounds are highly reliable and have high hole-transport properties to contribute to a reduction in drive voltage.

Specifically, the following examples can be given: 4-phenyl-4'-(9-phenyl-9H-carbazol-3-yl)triphenylamine (abbreviation: PCBA1BP), 4,4'-diphenyl-4"-(9-phenyl-9H-carbazol-3-yl)triphenylamine (abbreviation: PCBBi1BP), 4-(1-naphthyl)-4'-(9-phenyl-9H-carbazol-3-yl)triphenylamine (abbreviation: PCBANB), 4,4'-di(L-naphthyl)-4"-(9-phenyl-9H-carbazol-3-yl)triphenylamine (abbreviation: PCBNBB), 9,9-dimethyl-N-phenyl-N-[4-(9-phenyl-9H-carbazol-3-yl)phenyl]fluoren-2-amine (abbreviation: PCBAF), N-phenyl-N-[4-(9-phenyl-9H-carbazol-3-yl)phenyl]spiro-9,9'-bifluoren-2-amine (abbreviation: PCBASF), 3-[N-(1-naphthyl)-N-(9-phenylcarbazol-3-yl)amino]-9-phenylcarbazole (abbreviation: PCzPCN1), 4,4',4"-tris[N-(1-naphthyl)-N-phenylamino]triphenylamine (abbreviation: 1'-TNATA), 2,7-bis[N-(4-diphenylaminophenyl)-N-phenylamino]spiro-9,9'-bifluorene (abbreviation: DPA2SF), N',N'-bis(9-phenylcarbazol-3-yl)-N',N'-diphenylbenzene-1,3-diamine (abbreviation: PCA2B), N-(9,9-dimethyl-2-diphenylamino-9H-fluoren-7-yl)diphenylamine (abbreviation: DPNF). N,N',N"-triphenyl-N,N',N"-tris(9-phenylcarbazol-3-yl)benzene-1,3,5-triamine (abbreviation: PCA3B), 2-[N-(9-phenylcarbarol-3-yl)-N-phenylamino]spiro-9,9'-bitluorene (abbreviation: PCASF), 2-[N-(4-diphenylaminophenyl)-N-phenylamino]spiro-9,9'-bifluorene (abbreviation: DPASF), N,N'-bis[4-(carbazol-9-yl)phenyl]-N,N'-diphenyl-9,9-dimethylfluorene-2,7-diamine (abbreviation: YGA2F), N,N'-bis(3-methylphenyl)-N,N'-diphenyl-[1,1'-biphenyl]-4,4'-diamine (abbreviation: TPD), 4,4'-bis[N-(4-diphenylaminophenyl)-N-phenylamino]biphenyl (abbreviation: DPAB), N-(9,9-dimethyl-9H-fluoren-2-yl)-N-{9,9-dimethyl-2-[N'-phenyl-N'-(9,9-dimethyl-9H-fluoren-2-yl)amino]-9H-fluoren-7-yl}phenylamine (abbreviation: DFLADFL), 3-[N-(9-phenylcarbazol-3-yl)-N-phenylamino]-9-phenylcarbarole (abbreviation: PCzPICA1), 3,6-bis[N-(9-phenylcarbazol-3-yl)-N-phenylamino]-9-phenyl-carbazole (abbreviation: PCzPCA2), 3-[N-(4-diphenylaminophenyl)-N-phenylamino]-9-phenylcarbazole (abbreviation: PCZDPA1), 3,6-bis[N-(4-diphenylaminophenyl)-N-phenylamino]-9-phenylcarbazole (abbreviation: PCzDPA2), 4,4'-bis(N-{4-[N'-(3-methylphenyl)-N'-phenylamino]phenyl}-N-phenylamino)biphenyl (abbreviation: DNTPD), and 3,6-bis[N-(4-diphenylaminophenyl)-N-(1-naphthyl)amino]-9-phenylcarbarole (abbreviation: PCzTPN2).

The following examples can also be given: aromatic amine compounds such as 4,4'-bis[N-(1-naphthyl)-N-phenylamino]biphenyl (abbreviation: NPB or α-NPD), 4,4',4"-tris(N,N-diphenylamino)triphenylamine (abbreviation: TDATA), 4,4',4"-tris(N-(3-methylphenyl)-N-phenylamino)triphenylamine (abbreviation: MTDATA), 4,4'-bis[N-(spiro-9,9'-bifluoren-2-yl)-N-phenylamino]biphenyl (abbreviation: BSPB), 4,4',4"-tris(N-carbazolyl)triphenylamine (abbreviation: TCTA), 4-phenyl-4'-(9-phenylfluoren-9-yl)triphenylamine (abbreviation: BPAFLP), 4-phenyl-3'-(9-phenylfluoren-9-yl)triphenylamine (abbreviation: mBPAFLP), and 4,4'-bis[N-(9,9-dimethylfluoren-2-yl)-N-phenylamino]biphenyl (abbreviation: DFLDPBi): and carbazole derivatives such as 1,3-bis(N-carbazolyl)benzene (abbreviation: mCP), 4,4'-di (N-carbazolyl)biphenyl (abbreviation: CBP), 3,6-bis(3,5-diphenylphenyl)-9-phenylcarbazole (abbreviation: CzTP), 3,3'-bis(9-phenyl-9H-carbazole) (abbreviation: PCCP), CzPA, and PCzPA. In addition, high molecular compounds such as poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl)methacrylamide] (abbreviation: PTPDMA), and poly[N,N'-bis(4-butylphenyl)-N,N'-bis(phenyl)benzidine] (abbreviation: Poly-TPD).

As other examples, compounds having thiophene skeletons, such as 4,4',4''-(1,3,5-benzenetriyl)tri(dibenzothiophene) (abbreviation: DBT3P-II), 2,8-diphenyl-4-[4-(9-phenyl-9H-fluoren-9-yl)phenyl]dibenzothiophene (abbreviation: DBTFLP-III), and 4-[4-(9-phenyl-9H-fluoren-9-yl)phenyl]-6-phenyldibenzothiophene (abbreviation: DBTFLP-IV), and compounds having furan skeletons, such as 4,4',4''-(1,3,5-benzenetriyl)tri(dibenzofuran) (abbreviation: DBF3P-II) and 4-{3-[3-(9-phenyl-9H-fluoren-9-yl)phenyl]phenyl}dibenzofuran (abbreviation: mmDBFFLBi-II) can be given.

Here, for improvement in efficiency of energy transfer from a host material to a guest material, the Förster mechanism (dipole-dipole interaction) and the Dexter mechanism (electron exchange interaction), which are known as mechanisms of energy transfer between molecules, are considered. According to the mechanisms, it is preferable that an emission spectrum of a host material (fluorescence spectrum in energy transfer from a singlet excited state, phosphorescence spectrum in energy transfer from a triplet excited state) have a large overlap with an absorption spectrum of a guest material (specifically, spectrum in an absorption band on the longest wavelength (lowest energy) side).

However, in general, it is difficult to obtain an overlap between a fluorescence spectrum of a host material and an absorption spectrum in an absorption band on the longest wavelength (lowest energy) side of a guest material. The reason for this is as follows: if the fluorescence spectrum of the host material overlaps with the absorption spectrum in the absorption band on the longest wavelength (lowest energy) side of the guest material, since a phosphorescence spectrum of the host material is located on a long wavelength (low energy) side as compared to the fluorescence spectrum, the $T_1$ level of the host material becomes lower than the $T_1$ level of the guest material and the above-described problem of quenching occurs: yet, when the host material is designed in such a manner that the $T_1$ level of the host material is higher than the $T_1$ level of the guest material to avoid the problem of quenching, the fluorescence spectrum of the host material is shifted to the shorter wavelength (higher energy) side, and thus the fluorescence spectrum does not have any overlap with the absorption spectrum in the absorption band on the longest wavelength (lowest energy) side of the guest material. For that reason, in general, it is difficult to obtain an overlap between a fluorescence spectrum of a host material and an absorption spectrum in an absorption band on the longest wavelength (lowest energy) side of a guest material so as to maximize energy transfer from a singlet excited state of a host material.

Thus, it is preferable that the light-emitting layer of the light-emitting element of one embodiment of the present invention contain a carrier-transport compound in addition to the phosphorescent compound and the host material, and a combination of the host material and the carrier-transport compound form an exciplex (also referred to as excited complex). In that case, the host material and the carrier-transport compound form an exciplex at the time of recombination of carriers (electrons and holes) in the light-emitting layer. Thus, in the light-emitting layer, fluorescence spectra of the host material and the carrier-transport compound are converted into an emission spectrum of the exciplex which is located on a longer wavelength side. Moreover, when the host material and the carrier-transport compound are selected such that the emission spectrum of the exciplex has a large overlap with the absorption spectrum of the guest material, energy transfer from a singlet excited state can be maximized. Note that also in the case of a triplet excited state, energy transfer from the exciplex, not the host material, is assumed to occur. In one embodiment of the present invention to which such a structure is applied, energy transfer efficiency can be improved owing to energy transfer utilizing an overlap between an emission spectrum of an exciplex and an absorption spectrum of a phosphorescent compound; accordingly, a light-emitting element with high external quantum efficiency can be provided.

A combination of the host material and the carrier-transport compound at least forms an exciplex; for example, one of the host material and the carrier-transport compound is an electron-transport compound and the other is a hole-transport compound. As the electron-transport compound and the hole-transport compound, for example, the above-described materials can be used. The materials which can be used as the host material or the carrier-transport compound are not limited to the above materials as long as a combination of the material used as the host material and the material used as the carrier-transport compound can form an exciplex, an emission spectrum of the exciplex overlaps with an absorption spectrum of the guest material, and a peak of the emission spectrum of the exciplex is located on a longer wavelength side than a peak of the absorption spectrum of the guest material.

Note that a carrier balance may be controlled by adjusting the mixture ratio of the host material to the carrier-transport compound, which is preferably from 1:9 to 9:1.

Further, the exciplex may be formed at the interface between two layers. For example, when a layer containing the electron-transport compound and a layer containing the hole-transport compound are stacked, the exciplex is formed in the vicinity of the interface thereof. These two layers may be used as the light-emitting layer in the light-emitting element of one embodiment of the present invention. In that case, the phosphorescent compound may be added to the vicinity of the interface. The phosphorescent compound may be added to one of the two layers or both.

<Hole-Transport Layer>

The hole-transport layer 202 is a layer that contains a hole-transport substance.

The hole-transport substance is a substance with a property of transporting more holes than electrons, and is especially preferably a substance with a hole mobility of $10^{-6}$ cm$^2$/Vs or more.

For the hole-transport layer 202, it is possible to use any of the hole-transport compounds that are described as examples of the substance applicable to the light-emitting layer.

Further, an aromatic hydrocarbon compound such as CzPA, t-BuDNA, DNA, or DPAnth can be used.

<Electron-Transport Layer>

The electron-transport layer 204 contains an electron-transport substance.

The electron-transport substance is a substance having a property of transporting more electrons than holes, and is especially preferably a substance with an electron mobility of $10^{-6}$ cm$^2$/Vs or more.

For the electron-transport layer 204, it is possible to use any of the electron-transport compounds that are described as examples of the substance applicable to the light-emitting layer.

The electron-transport layer may have a stacked-layer structure including a first electron-transport layer on the anode side and a second electron-transport layer on the cathode side. In that case, the first electron-transport layer being in contact with the light-emitting layer that is the closest to the cathode preferably contains a substance having an anthracene skeleton or a substance having an anthracene skeleton and a carbazole skeleton. In a light-emitting element including this structure, a deterioration rate can be slow and a voltage increase due to driving can be small (i.e., an internal resistance increase due to driving can be small).

In general, design is performed such that the LUMO level of a host material is shallower than that of a material of an electron-transport layer and that the LUMO level of the material of the electron-transport layer is shallower than that of a material of an electron-injection layer in order that electron injection from a cathode to a light-emitting layer can be smoothly performed to prevent deterioration due to injection of electrons going over a high barrier and to reduce drive voltage. However, the light-emitting element of one embodiment of the present invention has a major characteristic in that deterioration can be prevented even when the substance with an anthracene skeleton used in the electron-transport layer has the deepest LUMO level. It is needless to say that deterioration can be prevented also when the substance with an anthracene skeleton has a LUMO level substantially equal to that of the host material or the material of the electron-injection layer or when the substance with an anthracene skeleton has a LUMO level between those of the material of the electron-injection layer and the host material as described above.

As a substance having an anthracene skeleton, for example, CzPA, 7-[4-(10-phenyl-9-anthryl)phenyl]-7H-dibenzo[c,g]carbazole (abbreviation: cgDBCzPA), 4-[3-(9,10-diphenyl-2-anthryl)phenyl]dibenzofuran (abbreviation: 2mDBFPPA-II), 6-[3-(9,10-diphenyl-2-anthryl)phenyl]-benzo[b]naphtho[1,2-d]furan (abbreviation: 2mBnfPPA), or the like can be favorably used.

When a substance having an anthracene skeleton is used for the first electron-transport layer, the second electron-transport layer contains an organic compound. An electron-transport substance can be used as the organic compound. In view of drive voltage, the LUMO level of the organic compound contained in the second electron-transport layer is preferably deeper than that of the substance used as the host material. Note that when used as a main material of an electron-transport layer, what is called an aromatic hydrocarbon, which does not have a hetero ring and consists only of an aromatic condensed ring, prevents a light-emitting element from carrying out its function. That is, when an electron-transport layer in contact with a cathode or an electron-injection layer has a single-layer structure and is formed using a substance having an anthracene skeleton, electrons are not easily injected from the cathode to the electron-transport layer because anthracene is an aromatic hydrocarbon. Thus, when a substance having an anthracene skeleton is used for the first electron-transport layer, the second electron-transport layer needs to be provided between the first electron-transport layer and the cathode. The organic compound used for the second electron-transport layer is required to accept electrons easily from the cathode and not to form a high barrier against electron injection to the first electron-transport layer including the substance having an anthracene skeleton. In order that the organic compound used for the second electron-transport layer can easily accept electrons from the cathode, the organic compound is preferably a π-electron deficient heteroaromatic compound, examples of which include a heteroaromatic compound having a heteroaromatic ring with a pyridine skeleton, a heteroaromatic compound having a heteroaromatic ring with a phthalazine skeleton, a heteroaromatic compound having a heteroaromatic ring with a pyrimidine skeleton, a heteroaromatic compound having a heteroaromatic ring with a pyrazine skeleton, and a heteroaromatic compound having a heteroaromatic ring with a triazine skeleton. Among specific examples of these heteroaromatic rings, which include a pyridine skeleton, a pyrimidine skeleton, a quinoline skeleton, a quinoxaline skeleton, and a dibenzo[f,h]quinoxaline skeleton, a bipyridine skeleton is particularly effective. As a bipyridine skeleton, 2,2'-bipyridine and a phenanthroline are preferable. Further, to lower a barrier against electron injection to the first electron-transport layer, it is preferable that the LUMO level of the organic compound used for the second electron-transport layer be substantially equal to or shallower than that of the substance with an anthracene skeleton used for the first electron-transport layer. Note that the LUMO level of the organic compound is preferably deeper than that of the host material, as already described.

Examples of an organic compound that can be favorably used for the second electron-transport layer include Alq, BAlq, BCP, BPhen, 2,9-bis(naphthalen-2-yl)-4,7-diphenyl-1,10-phenanthroline (abbreviation: NBphen), BP4mPy, 2,2'-[2,2'-bipyridine-5,6-diylbis(biphenyl-4,4'-diyl)]bisbenzoxazole (abbreviation: BOxP2BPy).

<Hole-Injection Layer>

The hole-injection layer 201 is a layer containing a hole-injection substance.

Examples of the hole-injection substance include metal oxides such as molybdenum oxide, titanium oxide, vanadium oxide, rhenium oxide, ruthenium oxide, chromium oxide, zirconium oxide, hafnium oxide, tantalum oxide, silver oxide, tungsten oxide, and manganese oxide.

Alternatively, a phthalocyanine-based compound such as phthalocyanine (abbreviation: H$_2$Pc) or copper(II) phthalocyanine (abbreviation: CuPc) can be used.

Further alternatively, it is possible to use an aromatic amine compound such as TDATA, MTDATA, DPAB, DNTPD, 1,3,5-tris[N-(4-diphenylaminophenyl)-N-phenylamino]benzene (abbreviation: DPA3B), PCzPCA1, PCzPCA2, or PCzPCN1.

Further alternatively, it is possible to use a high molecular compound such as PVK, PVTPA, PTPDMA, or Poly-TPD, or a high molecular compound to which acid is added, such as poly(3,4-ethylenedioxythiophene)/poly(styrenesulfonic acid) (PEDOT/PSS) or polyaniline/poly(styrenesulfonic acid) (PAni/PSS).

The hole-injection layer 201 may serve as the charge-generation region. When the hole-injection layer 201 in contact with the anode serves as the charge-generation region, any of a variety of conductive materials can be used for the anode regardless of their work functions. Materials contained in the charge-generation region will be described later.

<Electron-Injection Layer>

The electron-injection layer 205 contains an electron-injection substance.

Examples of the electron-injection substance include an alkali metal, an alkaline earth metal, a rare earth metal, and a compound thereof (e.g., an oxide thereof, a carbonate thereof, and a halide thereof), such as lithium, cesium, calcium, lithium oxide, lithium carbonate, cesium carbonate, lithium fluoride, cesium fluoride, calcium fluoride, and erbium fluoride.

The electron-injection layer 205 may serve as the charge-generation region. When the electron-injection layer 205 in contact with the cathode serves as the charge-generation region, any of a variety of conductive materials can be used for the cathode regardless of their work functions. Materials contained in the charge-generation region will be described later.

<Charge-Generation Region>

A charge-generation region included in a hole-injection layer or an electron-injection layer and the charge-generation region 107 may have either a structure in which an electron acceptor (acceptor) is added to a hole-transport substance or a structure in which an electron donor (donor) is added to an electron-transport substance. Alternatively, these structures may be stacked.

The hole-transport compounds and the electron-transport compounds which are described as examples of the substance that can be used for a light-emitting layer can be given as the hole-transport substance and the electron-transport substance.

Further, as the electron acceptor, 7,7,8,8-tetracyano-2,3,5, 6-tetrafluoroquinodimethane (abbreviation: $F_4$-TCNQ), chloranil, and the like can be given. In addition, a transition metal oxide can be given. In addition, an oxide of metals that belong to Group 4 to Group 8 of the periodic table can be given. Specifically, vanadium oxide, niobium oxide, tantalum oxide, chromium oxide, molybdenum oxide, tungsten oxide, manganese oxide, and rhenium oxide are preferable since their electron-accepting property is high. Among these, molybdenum oxide is especially preferable because it is stable in the air, has a low hygroscopic property, and is easily handled.

Further, as the electron donor, it is possible to use an alkali metal, an alkaline earth metal, a rare earth metal, a metal belonging to Group 13 of the periodic table, or an oxide or a carbonate thereof. Specifically, lithium, cesium, magnesium, calcium, ytterbium, indium, lithium oxide, cesium carbonate, or the like is preferably used. Alternatively, an organic compound such as tetrathianaphthacene may be used as the electron donor.

The above-described layers included in the EL layer 103 and the charge-generation region 107 can be formed separately by any of the following methods: an evaporation method (including a vacuum evaporation method), a transfer method, a printing method, an inkjet method, a coating method, and the like.

A light-emitting element in this embodiment is preferably fabricated over a substrate of glass, plastic, or the like. As the way of stacking layers over the substrate, layers may be sequentially stacked from the first electrode 101 side or sequentially stacked from the second electrode 105 side. In a light-emitting device, although one light-emitting element may be formed over one substrate, a plurality of light-emitting elements may be formed over one substrate. With a plurality of light-emitting elements as described above formed over one substrate, a lighting device in which elements are separated or a passive-matrix light-emitting device can be manufactured. A light-emitting element may be formed over an electrode electrically connected to a thin film transistor (TFT), for example, which is formed over a substrate of glass, plastic, or the like, so that an active matrix light-emitting device in which the TFT controls the driving of the light-emitting element can be manufactured. Note that there is no particular limitation on the structure of the TFT, which may be a staggered TFT or an inverted staggered TFT. In addition, crystallinity of a semiconductor used for the TFT is not particularly limited either; an amorphous semiconductor or a crystalline semiconductor may be used. In addition, a driver circuit formed in a TFT substrate may be formed with an n-type TFT and a p-type TFT, or with either an n-type TFT or a p-type TFT.

With the use of a light-emitting element described in this embodiment, a passive matrix light-emitting device or an active matrix light-emitting device in which driving of the light-emitting element is controlled by a transistor can be manufactured. Furthermore, the light-emitting device can be applied to an electronic device, a lighting device, or the like.

The above-described light-emitting element of one embodiment of the present invention has high emission efficiency, a long lifetime, and high reliability. Furthermore, in the light-emitting element of one embodiment of the present invention, light emissions from a plurality of light-emitting substances can be obtained. The light-emitting element of one embodiment of the present invention does not have a tandem structure, and thus its manufacturing process is not complicated and the amount of power loss due to an intermediate layer is small. In addition, the light-emitting element has a high utility value as a white light-emitting element.

This embodiment can be freely combined with any of other embodiments.

Embodiment 2

In this embodiment, a light-emitting device of one embodiment of the present invention will be described with reference to FIGS. 4A and 4B and FIGS. 5A and 5B. The light-emitting device in this embodiment includes the light-emitting element of one embodiment of the present invention. Since the light-emitting element has a long lifetime, a light-emitting device having high reliability can be provided.

Figure 4A:
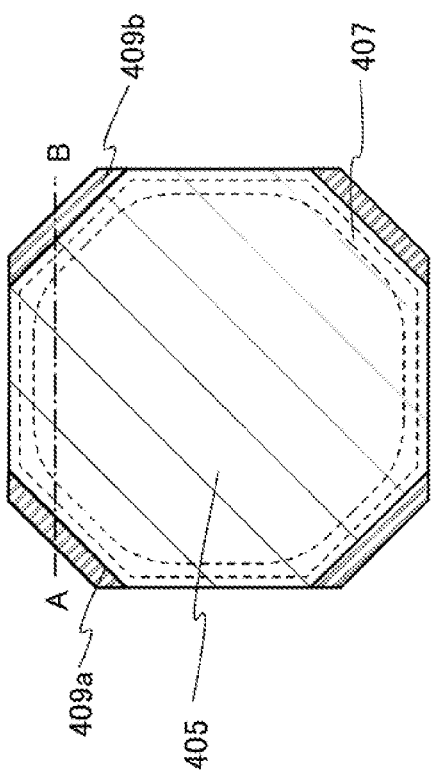
FIGS. 4A and 4B illustrate an example of a light-emitting device of one embodiment of the present invention.
Figure 4B:
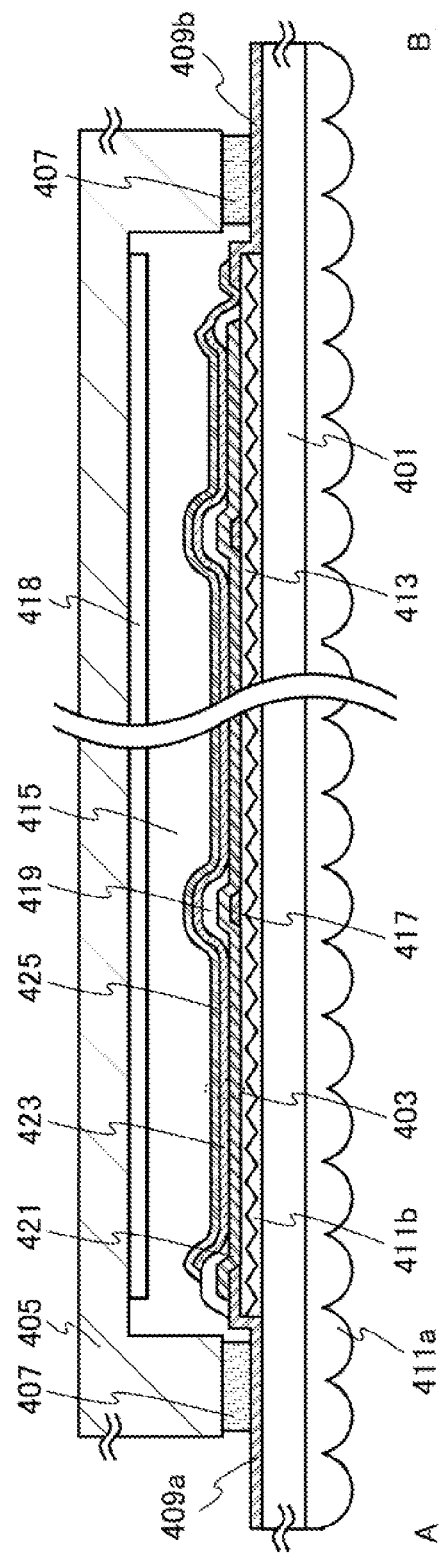

FIG. 4A is a plan view of a light-emitting device of one embodiment of the present invention, and FIG. 4B is a cross-sectional view taken along dashed-dotted line A-B in FIG. 4A.

In the light-emitting device in this embodiment, a light-emitting element 403 is provided in a space 415 surrounded by a support substrate 401, a sealing substrate 405, and a sealing material 407. The light-emitting element 403 is a light-emitting element having a bottom-emission structure: specifically, a first electrode 421 which transmits visible light is provided over the support substrate 401, an EL layer 423 is provided over the first electrode 421, and a second electrode 425 is provided over the EL layer 423. The light-emitting element 403 is a light-emitting element to which one embodiment of the present invention in Embodiment 1 is applied. The sealing substrate 405 includes a drying agent 418 on the light-emitting element 403 side.

A first terminal 409a is electrically connected to an auxiliary wiring 417 and the first electrode 421. An insulating layer 419 is provided over the first electrode 421 in a region which overlaps with the auxiliary wiring 417. The first terminal 409a is electrically insulated from the second electrode 425 by the insulating layer 419. A second terminal 409b is electrically connected to the second electrode 425. Note that although the first electrode 421 is formed over the auxiliary wiring 417 in this embodiment, the auxiliary wiring 417 may be formed over the first electrode 421.

A light extraction structure 411a is preferably provided at the interface between the support substrate 401 and the atmosphere. When provided at the interface between the support substrate 401 and the atmosphere, the light extraction structure 411a can reduce light which cannot be extracted to the atmosphere due to total reflection, resulting in an increase in the light extraction efficiency of the light-emitting device.

In addition, a light extraction structure 411b is preferably provided at the interface between the light-emitting element 403 and the support substrate 401. When the light extraction structure 411b has unevenness, a planarization layer 413 is preferably provided between the light extraction structure 411b and the first electrode 421. Accordingly, the first electrode 421 can be a flat film, and generation of leakage current in the EL layer 423 due to the unevenness of the first electrode 421 can be prevented. Further, because of the light extraction structure 411b at the interface between the planarization layer 413 and the support substrate 401, light which cannot be extracted to the atmosphere due to total reflection can be reduced, so that the light extraction efficiency of the light-emitting device can be increased.

The surface of the planarization layer 413 which is in contact with the first electrode 421 is flatter than the surface of the planarization layer 413 which is in contact with the light extraction structure 411b. As a material of the planarization layer 413, glass, a resin, or the like having a light-transmitting property and a high refractive index can be used.

FIG. 5A is a plan view of a light-emitting device of one embodiment of the present invention, and FIG. 5B is a cross-sectional view taken along dashed-dotted line C-D in FIG. 5A.

An active matrix light-emitting device in this embodiment includes, over a support substrate 501, a light-emitting portion 551, a driver circuit portion 552 (gate side driver circuit portion), a driver circuit portion 553 (source side driver circuit portion), and a sealing material 507. The light-emitting portion 551 and the driver circuit portions 552 and 553 are sealed in a space 515 surrounded by the support substrate 501, a sealing substrate 505, and the sealing material 507.

The light-emitting portion 551 fabricated by a color filter method is illustrated in FIG. 5B.

The light-emitting portion 551 includes a plurality of light-emitting units each including a switching transistor 541a, a current control transistor 541b, and a first electrode 521 electrically connected to a wiring (a source electrode or a drain electrode) of the current control transistor 541b.

A light-emitting element 503 included in the light-emitting portion 551 has a top-emission structure and includes a first electrode 521, an EL layer 523, and the second electrode 525 which transmits visible light. Further, a partition 519 is formed so as to cover an end portion of the first electrode 521.

Over the support substrate 501, a lead wiring 517 for connecting an external input terminal through which a signal (e.g., a video signal, a clock signal, a start signal, or a reset signal) or a potential from the outside is transmitted to the driver circuit portion 552 or 553 is provided. Here, an example is described in which a flexible printed circuit (FPC) 509 is provided as the external input terminal.

The driver circuit portions 552 and 553 include a plurality of transistors. FIG. 5B illustrates two of the transistors in the driver circuit portion 552 (transistors 542 and 543).

To prevent an increase in the number of manufacturing steps, the lead wiring 517 is preferably formed using the same material and the same step(s) as those of the electrode or the wiring in the light-emitting portion or the driver circuit portion. Described in this embodiment is an example in which the lead wiring 517 is formed using the same material and the same step(s) as those of the source electrodes and the drain electrodes of the transistors included in the light-emitting portion 551 and the driver circuit portion 552.

In FIG. 5B, the sealing material 507 is in contact with a first insulating layer 511 over the lead wiring 517. The adhesion of the sealing material 507 to metal is low in some cases. Therefore, the sealing material 507 is preferably in contact with an inorganic insulating film over the lead wiring 517. Such a structure enables a light-emitting device to have high sealing capability, high adhesion, and high reliability. Examples of the inorganic insulating film include oxide films of metals and semiconductors, nitride films of metals and semiconductors, and oxynitride films of metals and semiconductors, and specifically, a silicon oxide film, a silicon nitride film, a silicon oxynitride film, a silicon nitride oxide film, an aluminum oxide film, a titanium oxide film, and the like.

The first insulating layer 511 has an effect of preventing diffusion of impurities into a semiconductor included in the transistor. As the second insulating layer 513, an insulating film having a planarization function is preferably selected in order to reduce surface unevenness due to the transistor.

The sealing substrate 505 illustrated in FIG. 5B is provided with a color filter 533 as a coloring layer at a position overlapping with the light-emitting element 503 (a light-emitting region thereof), and is also provided with a black matrix 531 at a position overlapping with the partition 519. Further, an overcoat layer 535 is provided so as to cover the color filter 533 and the black matrix 531.

Examples of materials that can be used for the light-emitting device of one embodiment of the present invention will be described.

[Substrate]

The substrate on the side from which light from the light-emitting element is extracted is formed using a material which transmits the light. For example, a material such as glass, quartz, ceramics, sapphire, or an organic resin can be used. The substrate of a flexible light-emitting device is formed using a flexible material.

As the glass, for example, non-alkali glass, barium borosilicate glass, aluminoborosilicate glass, or the like can be used.

Examples of a material having flexibility and a light-transmitting property with respect to visible light include glass that is thin enough to have flexibility, polyester resins such as polyethylene terephthalate (PET) and polyethylene naphthalate (PEN), a polyacrylonitrile resin, a polyimide resin, a polymethyl methacrylate resin, a polycarbonate (PC) resin, a polyethersulfone (PES) resin, a polyamide resin, a cycloolefin resin, a polystyrene resin, a polyamide imide resin, and a polyvinyl chloride resin. In particular, a material whose thermal expansion coefficient is low is preferred, and for example, a polyamide imide resin, a polyimide resin, or PET can be suitably used. A substrate in which a glass fiber is impregnated with an organic resin or a substrate whose thermal expansion coefficient is reduced by mixing an organic resin with an inorganic filler can also be used. A substrate using such a material is lightweight, and thus a light-emitting device using this substrate can also be lightweight.

Furthermore, since the substrate through which light emission is not extracted does not need to have a light-transmitting property, a metal substrate using a metal material or an alloy material or the like can be used in addition to the above-mentioned substrates. A metal material and an alloy material, which have high thermal conductance, are preferred in that they can easily conduct heat into the whole sealing substrate and accordingly can reduce a local rise in the temperature of the light-emitting device. To obtain flexibility and bendability, the thickness of a metal substrate is preferably greater than or equal to 10 μm and less than or equal to 200 μm, further preferably greater than or equal to 20 μm and less than or equal to 50 μm.

There is no particular limitation on a material of the metal substrate, but it is preferable to use, for example, aluminum, copper, nickel, a metal alloy such as an aluminum alloy or stainless steel.

It is possible to use a substrate subjected to insulation treatment in such a manner that a surface of the conductive substrate is oxidized or an insulating film is formed on the surface. An insulating film may be formed by, for example, a coating method such as a spin-coating method and a dipping method, an electrodeposition method, an evaporation method, or a sputtering method. An oxide film may be formed over the substrate surface by an anodic oxidation method, exposing to or heating in an oxygen atmosphere, or the like.

The flexible substrate may have a stacked structure in which a hard coat layer (such as a silicon nitride layer) by which a surface of a light-emitting device is protected from damage, a layer (such as an aramid resin layer) which can disperse pressure, or the like is stacked over a layer of any of the above-mentioned materials. Furthermore, to suppress a decrease in lifetime of the light-emitting element due to moisture and the like, an insulating film with low water permeability may be provided. For example, a film containing nitrogen and silicon (e.g., a silicon nitride film, a silicon oxynitride film), or a film containing nitrogen and aluminum (e.g., an aluminum nitride film) may be provided.

The substrate may be formed by stacking a plurality of layers. When a glass layer is used, a barrier property against water and oxygen can be improved and thus a reliable light-emitting device can be provided.

For example, a substrate in which a glass layer, a bonding layer, and an organic resin layer are stacked from the side closer to a light-emitting element can be used. The thickness of the glass layer is greater than or equal to 20 μm and less than or equal to 200 μm, preferably greater than or equal to 25 μm and less than or equal to 100 μm. With such a thickness, the glass layer can have both a high barrier property against water and oxygen and flexibility. The thickness of the organic resin layer is greater than or equal to 10 μm and less than or equal to 200 μm, preferably greater than or equal to 20 μm and less than or equal to 50 μm. By providing such an organic resin layer on an outer side than the glass layer, occurrence of a crack or a break in the glass layer can be suppressed and mechanical strength can be improved. With the substrate that includes such a composite material of a glass material and an organic resin, a highly reliable and flexible light-emitting device can be provided.

[Insulating Film]

An insulating film may be provided between the supporting substrate and the light-emitting element or between the supporting substrate and the transistor. The insulating film can be formed using an inorganic insulating material such as silicon oxide, silicon nitride, silicon oxynitride, or silicon nitride oxide. In order to suppress entry of moisture or the like into the transistor and the light-emitting element, it is particularly preferable to use an insulating film with low water permeability such as a silicon oxide film, a silicon nitride film, or an aluminum oxide film. For a similar purpose and with a similar material, an insulating film covering the transistor and the light-emitting element may be provided.

[Light-Emitting Element]

The light emitting device of one embodiment of the present invention includes at least one light emitting element described in Embodiment 1.

[Partition]

For the partition, an organic resin or an inorganic insulating material can be used. As the organic resin, for example, a polyimide resin, a polyamide resin, an acrylic resin, a siloxane resin, an epoxy resin, a phenol resin, or the like can be used. As the inorganic insulating material, silicon oxide, silicon oxynitride, or the like can be used. In particular, a photosensitive resin is preferably used for easy formation of the partition.

There is no particular limitation on the method for forming the partition. A photolithography method, a sputtering method, an evaporation method, a droplet discharging method (e.g., an inkjet method), a printing method (e.g., a screen printing method or an offset printing method), or the like can be used.

[Auxiliary Wiring]

An auxiliary wiring is not necessarily provided; however, an auxiliary wiring is preferably provided because voltage drop due to the resistance of an electrode can be prevented.

For a material of the auxiliary wiring, a single layer or a stacked layer using a material selected from copper (Cu), titanium (Ti), tantalum (Ta), tungsten (W), molybdenum (Mo), chromium (Cr), neodymium (Nd), scandium (Sc), and nickel (Ni) or an alloy material including any of these materials as its main component is used. Aluminum can also be used as the material of the auxiliary wiring. When the auxiliary wiring of aluminum is provided to be in direct contact with a transparent oxide conductive material, aluminum might corrode; thus, in order to prevent corrosion, it is preferable that the auxiliary wiring have a stacked-layer structure and aluminum be used for a layer thereof which is not in contact with ITO or the like. The thickness of the auxiliary wiring can be greater than or equal to 0.1 μm and less than or equal to 3 μm, preferably greater than or equal to 0.1 μm and less than or equal to 0.5 μm.

When a paste (e.g., silver paste) is used as the material of the auxiliary wiring, a metal forming the auxiliary wiring aggregates in the form of particles, and as a result, the surface of the auxiliary wiring becomes rough and has many gaps. This makes it difficult for the EL layer to completely cover the auxiliary wiring, which is provided over the insulating layer 419, for example; accordingly, the upper electrode and the auxiliary wiring are easily connected electrically to each other, which is preferable.

[Sealing Material]

A method for sealing the light-emitting device is not limited, and either solid sealing or hollow sealing can be employed. For example, a glass material such as a glass frit or a resin material such as a two-component-mixture-type resin which is curable at room temperature, a light curable resin, or a thermosetting resin can be used. The light-emitting device may be filled with an inert gas such as nitrogen or argon, or a resin such as a polyvinyl chloride (PVC) resin, an acrylic resin, a polyimide resin, an epoxy resin, a silicone resin, a polyvinyl butyral (PVB) resin, or an ethylene vinyl acetate (EVA) resin. Further, a drying agent may be contained in the resin.

[Light Extraction Structure]

For the light extraction structure, a hemispherical lens, a micro lens array, a film provided with an uneven surface structure, a light diffusing film, or the like can be used. For example, a light extraction structure can be formed by attaching the lens or film to the substrate with an adhesive or the like which has substantially the same refractive index as the substrate or the lens or film.

[Transistor]

The light-emitting device of one embodiment of the present invention may include a transistor. The structure of the transistor is not limited: a top-gate transistor may be used, or a bottom-gate transistor such as an inverted staggered transistor may be used. An n-channel transistor may be used and a p-channel transistor may also be used. In addition, there is no particular limitation on a material used for the transistor. For example, a transistor in which silicon or an oxide semiconductor such as an In—Ga—Zn-based metal oxide is used in a channel formation region can be employed.

This embodiment can be combined with any of other embodiments, as appropriate.

Embodiment 3

In this embodiment, examples of electronic devices and lighting devices to which the light-emitting device of one embodiment of the present invention is applied will be described with reference to FIGS. 6A to 6E and FIGS. 7A and 7B.

Electronic devices in this embodiment each include the light-emitting device of one embodiment of the present invention in a display portion. Lighting devices in this embodiment each include the light-emitting device of one embodiment of the present invention in a light-emitting portion (a lighting portion). Highly reliable electronic devices and highly reliable lighting devices can be provided by adopting the light-emitting device of one embodiment of the present invention.

Examples of electronic devices to which the light-emitting device is applied are television devices (also referred to as TV or television receivers), monitors for computers and the like, cameras such as digital cameras and digital video cameras, digital photo frames, cellular phones (also referred to as mobile phones or portable telephone devices), portable game machines, portable information terminals, audio playback devices, large game machines such as pin-ball machines, and the like. Specific examples of these electronic devices and lighting devices are illustrated in FIGS. 6A to 6E and FIGS. 7A and 7B.

Figure 6A:
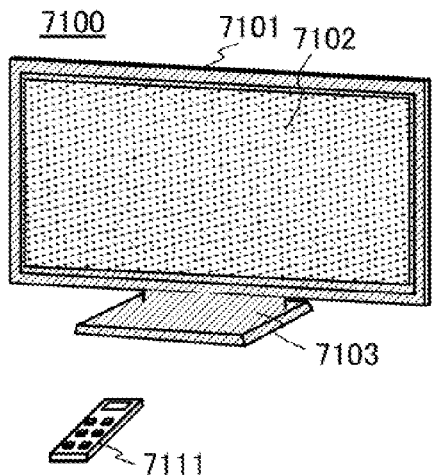
FIGS. 6A to 6E each illustrate an example of an electronic device of one embodiment of the present invention.

FIG. 6A illustrates an example of a television device. In a television device 7100, a display portion 7102 is incorporated in a housing 7101. The display portion 7102 is capable of displaying images. The light-emitting device of one embodiment of the present invention can be used for the display portion 7102. In addition, here, the housing 7101 is supported by a stand 7103.

The television device 7100 can be operated with an operation switch provided in the housing 7101 or a separate remote controller 7111. With operation keys of the remote controller 7111, channels and volume can be controlled and images displayed on the display portion 7102 can be controlled. The remote controller 7111 may be provided with a display portion for displaying data output from the remote controller 7111.

Note that the television device 7100 is provided with a receiver, a modem, and the like With the use of the receiver, general television broadcasting can be received. Moreover, when the television device is connected to a communication network with or without wires via the modem, one-way (from a transmitter to a receiver) or two-way (between a transmitter and a receiver or between receivers) information communication can be performed.

Figure 6B:
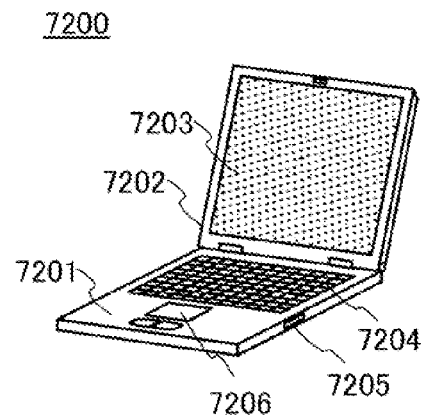

FIG. 6B illustrates an example of a computer. A computer 7200 includes a main body 7201, a housing 7202, a display portion 7203, a keyboard 7204, an external connection port 7205, a pointing device 7206, and the like. Note that this computer is manufactured by using the light-emitting device of one embodiment of the present invention for the display portion 7203.

Figure 6C:
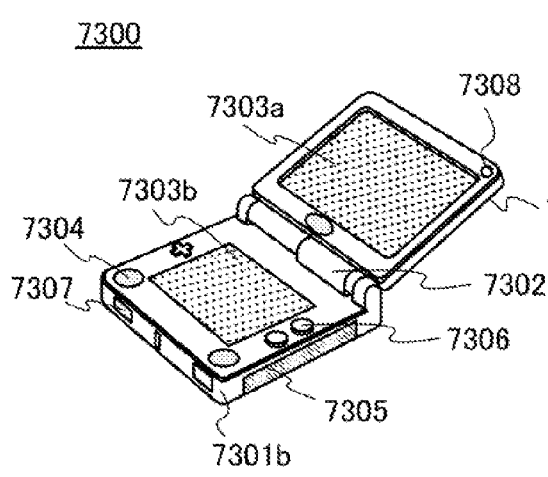

FIG. 6C illustrates an example of a portable game machine. A portable game machine 7300 has two housings, a housing 7301a and a housing 7301b, which are connected with a joint portion 7302 so that the portable game machine can be opened or closed. The housing 7301a incorporates a display portion 7303a, and the housing 7301b incorporates a display portion 7303b. In addition, the portable game machine illustrated in FIG. 6C includes a speaker portion 7304, a recording medium insertion portion 7305, an operation key 7306, a connection terminal 7307, a sensor 7308 (a sensor having a function of measuring or sensing force, displacement, position, speed, acceleration, angular velocity, rotational frequency, distance, light, liquid, magnetism, temperature, chemical substance, sound, time, hardness, electric field, electric current, voltage, electric power, radiation, flow rate, humidity, gradient, oscillation, odor, or infrared rays), an LED lamp, a microphone, and the like. It is needless to say that the structure of the portable game machine is not limited to the above structure as long as the light-emitting device of one embodiment of the present invention is used for at least either the display portion 7303a or the display portion 7303b, or both, and may include other accessories as appropriate. The portable game machine illustrated in FIG. 6C has a function of reading out a program or data stored in a recoding medium to display it on the display portion, and a function of sharing information with another portable game machine by wireless communication. Note that functions of the portable game machine illustrated in FIG. 6C are not limited to them, and the portable game machine can have various functions.

Figure 6D:
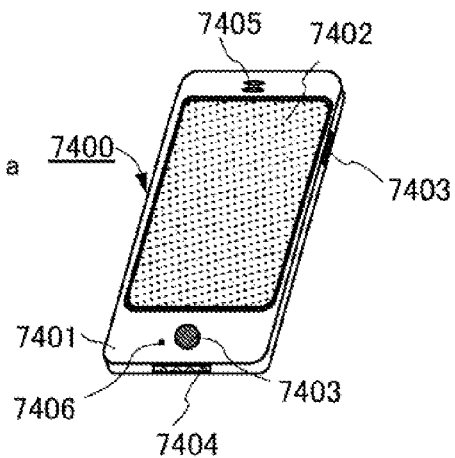

FIG. 6D illustrates an example of a cellular phone. A cellular phone 7400 is provided with a display portion 7402 incorporated in a housing 7401, an operation button 7403, an external connection port 7404, a speaker 7405, a microphone 7406, and the like. Note that the cellular phone 7400 is manufactured by using the light-emitting device of one embodiment of the present invention for the display portion 7402.

When the display portion 7402 of the cellular phone 7400 illustrated in FIG. 6D is touched with a finger or the like, data can be input into the cellular phone. Further, operations such as making a call and creating e-mail can be performed by touching the display portion 7402 with a finger or the like.

There are mainly three screen modes of the display portion 7402. The first mode is a display mode mainly for displaying an image. The second mode is an input mode mainly for inputting information such as characters. The third mode is a display-and-input mode in which two modes of the display mode and the input mode are combined.

For example, in the case of making a call or creating e-mail, an input mode mainly for inputting characters is selected for the display portion 7402 so that characters displayed on the screen can be input.

When a sensing device including a sensor such as a gyroscope sensor or an acceleration sensor for detecting inclination is provided inside the cellular phone 7400, display on the screen of the display portion 7402 can be automatically changed in direction by determining the orientation of the cellular phone 7400 (whether the cellular phone 7400 is placed horizontally or vertically for a landscape mode or a portrait mode).

The screen modes are changed by touch on the display portion 7402 or operation with the operation button 7403 of the housing 7401. The screen modes can be switched depending on the kind of images displayed on the display portion 7402. For example, when a signal of an image displayed on the display portion is a signal of moving image data, the screen mode is switched to the display mode. When the signal is a signal of text data, the screen mode is switched to the input mode.

Moreover, in the input mode, if a signal detected by an optical sensor in the display portion 7402 is detected and the input by touch on the display portion 7402 is not performed for a certain period, the screen mode may be controlled so as to be changed from the input mode to the display mode.

The display portion 7402 may function as an image sensor. For example, an image of a palm print, a fingerprint, or the like is taken by the display portion 7402 while in touch with the palm or the finger, whereby personal authentication can be performed. Further, when a backlight or a sensing light source which emits near-infrared light is provided in the display portion, an image of a finger vein, a palm vein, or the like can be taken.

Figure 6E:
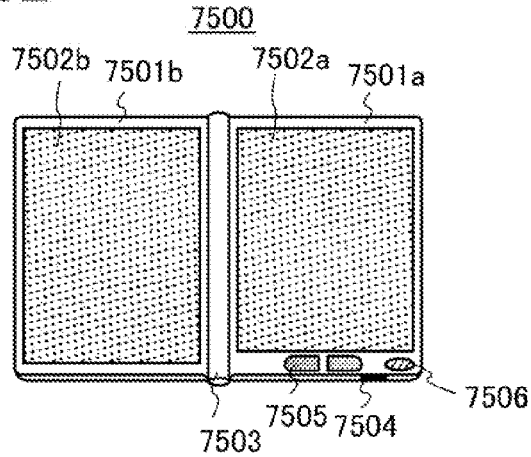

FIG. 6E illustrates an example of a foldable tablet terminal (in an open state). A tablet terminal 7500 includes a housing 7501a, a housing 7501b, a display portion 7502a, and a display portion 7502b. The housing 7501a and the housing 7501b are connected by a hinge 7503 and can be opened and closed using the hinge 7503 as an axis. The housing 7501a includes a power switch 7504, operation keys 7505, a speaker 7506, and the like. Note that the tablet terminal 7500 is manufactured by using the light-emitting device of one embodiment of the present invention for either the display portion 7502a or the display portion 7502b, or both.

At least part of the display portion 7502a or the display portion 7502b can be used as a touch panel region, where data can be input by touching displayed operation keys. For example, a keyboard can be displayed on the entire region of the display portion 7502a so that the display portion 7502a is used as a touch panel, and the display portion 7502b can be used as a display screen.

Figure 7A:
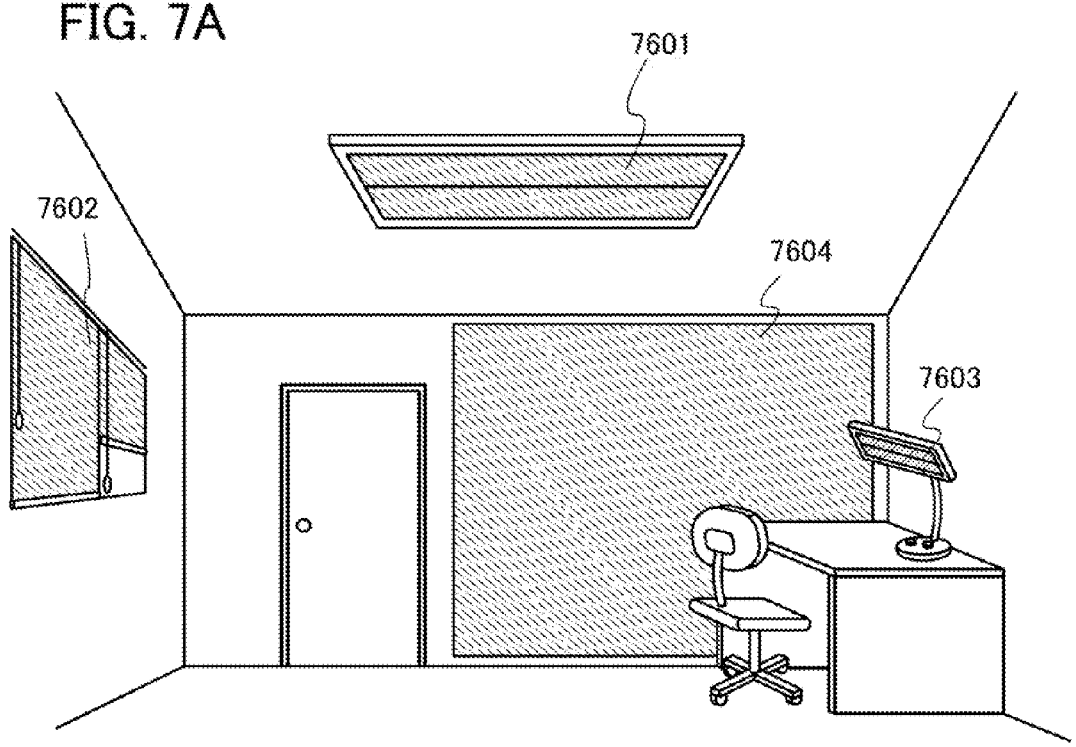
FIGS. 7A and 7B illustrate examples of a lighting device of one embodiment of the present invention.

An indoor lighting device 7601, a roll-type lighting device 7602, a desk lamp 7603, and a planar lighting device 7604 illustrated in FIG. 7A are each an example of a lighting device which includes the light-emitting device of one embodiment of the present invention. Since the light-emitting device of one embodiment of the present invention can have a larger area, it can be used as a large-area lighting device. Further, since the light-emitting device of one embodiment of the present invention is thin, the light-emitting device can be mounted on a wall.

Figure 7B:
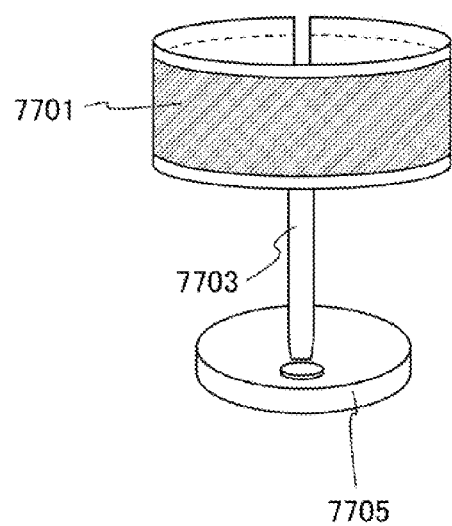

A desk lamp illustrated in FIG. 7B includes a lighting portion 7701, a support 7703, a support base 7705, and the like. The light-emitting device of one embodiment of the present invention is used for the lighting portion 7701. In one embodiment of the present invention, a lighting device whose light-emitting portion has a curved surface or a lighting device including a flexible lighting portion can be achieved. Such use of a flexible light-emitting device for a lighting device enables a place having a curved surface, such as a ceiling or a dashboard of a motor vehicle, to be provided with the lighting device, as well as increases the degree of freedom in design of the lighting device.

This embodiment can be combined with any of other embodiments, as appropriate.

Example 1

Figure 8:
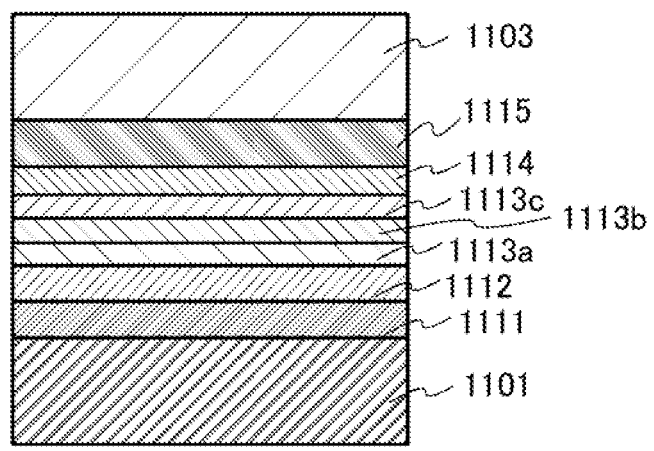
FIG. 8 illustrates a light-emitting element of Examples.

In this example, a light-emitting element of one embodiment of the present invention will be described with reference to FIG. 8. Chemical formulae of materials used in this example are shown below.

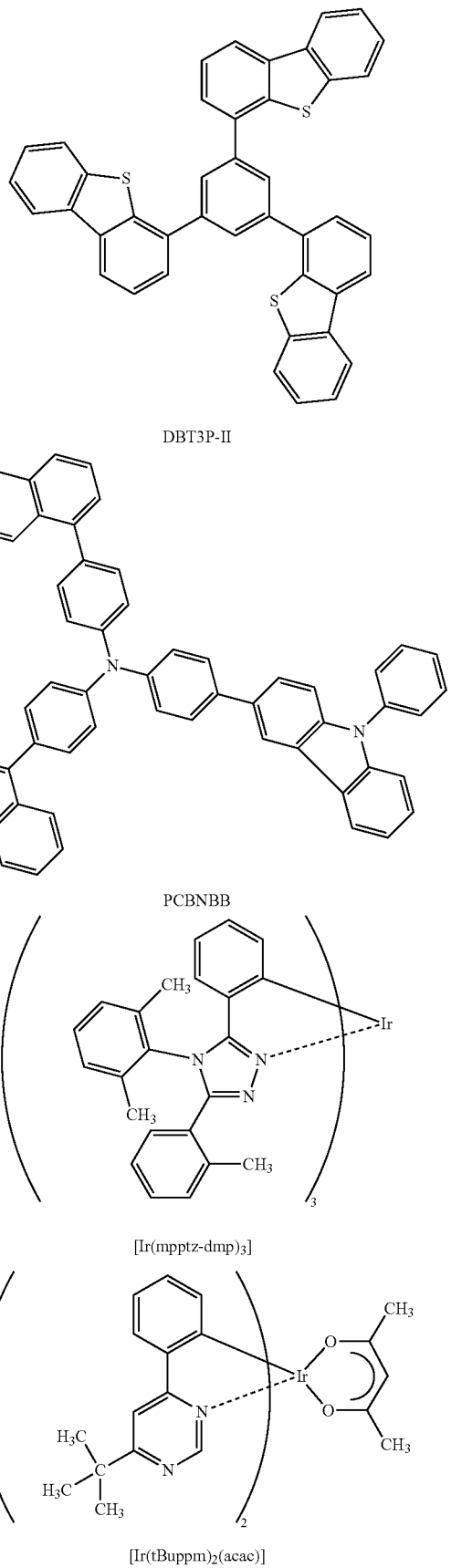

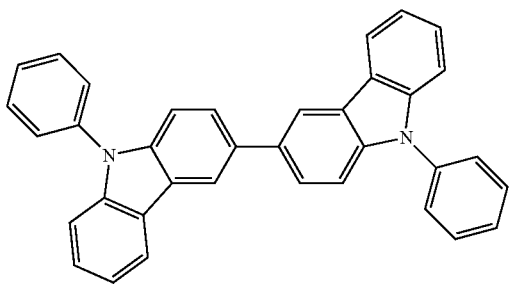

PCCP

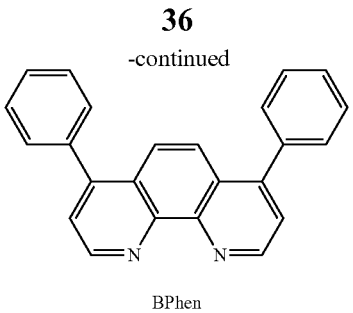

BPhen

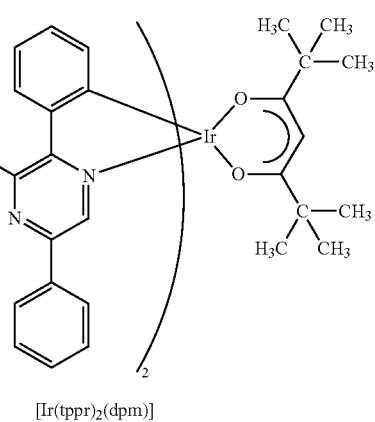

[Ir(tppr)₂(dpm)]

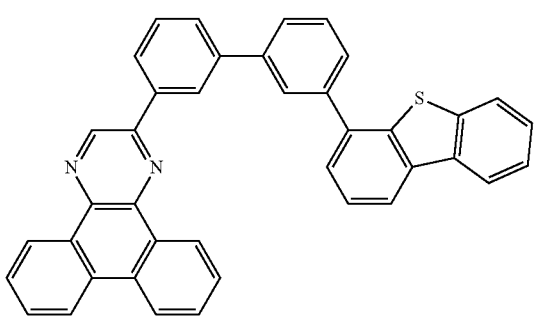

2mDBTBPDBq-II

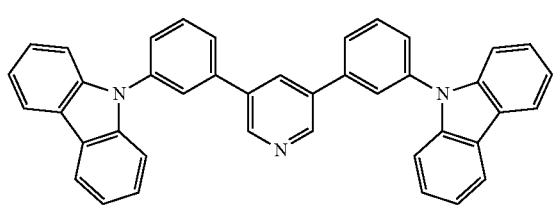

3,5DCzPPy

Light-emitting elements of this example each include three light-emitting layers. In a light-emitting element 1, a green light-emitting layer, a red light-emitting layer, and a blue light-emitting layer are stacked from an anode side. In a comparative light-emitting element 2, a red light-emitting layer, a green light-emitting layer, and a blue light-emitting layer are stacked from an anode side. Methods for manufacturing the light-emitting element 1 and the comparative light-emitting element 2 of this example will be described below.

(Light-Emitting Element 1)

First, a film of indium tin oxide containing silicon oxide (ITSO) was formed over a glass substrate by a sputtering method, so that a first electrode 1101 was formed. Note that the thickness was set to 110 nm and the electrode area was set to 2 mm×2 mm. Here, the first electrode 1101 is an electrode that functions as an anode of the light-emitting element.

Then, as pretreatment for forming the light-emitting element over the substrate, UV ozone treatment was performed for 370 seconds after washing a surface of the substrate with water and baking the substrate at 200° C. for 1 hour.

After that, the glass substrate was transferred into a vacuum evaporation apparatus where the pressure had been reduced to approximately $10^{-4}$ Pa, and was subjected to vacuum baking at 170° C. for 30 minutes in a heating chamber of the vacuum evaporation apparatus, and then the glass substrate was cooled down for approximately 30 minutes.

Then, the glass substrate over which the first electrode 1101 was formed was fixed to a substrate holder provided in the vacuum evaporation apparatus so that the surface on which the first electrode 1101 was formed faced downward. The pressure in the vacuum evaporation apparatus was reduced to approximately $10^{-4}$ Pa. After that, over the first electrode 1101, 4,4',4"-(1,3,5-benzenetriyl)tri(dibenzothiophene) (abbreviation: DBT3P-II) and molybdenum (VI) oxide were deposited by co-evaporation by an evaporation method using resistance heating, so that a hole-injection layer 1111 was formed. The thickness of the hole-injection layer 111 was set to 40 nm, and the weight ratio of DBT3P-II to molybdenum oxide was adjusted to 2:1 (=DBT3P-II: molybdenum oxide). Note that the co-evaporation method refers to an evaporation method in which evaporation is carried out from a plurality of evaporation sources at the same time in one treatment chamber.

Next, a film of 4,4'-di(1-naphthyl)-4"-(9-phenyl-9-carbazol-3-yl)triphenylamine (abbreviation: PCBNBB) was formed to a thickness of 20 nm over the hole-injection layer 1111 to form a hole-transport layer 1112.

Next, 2-[3'-(dibenzothiophen-4-yl)biphenyl-3-yl]dibenzo [f,h]quinoxaline (abbreviation: 2mDBTBPDBq-II), 4,4'-di (1-naphthyl)-4"-(9-phenyl-9H-carbazol-3-yl)triphenylamine (abbreviation: PCBNBB), and (acetylacetonato)bis (6-tert-butyl-4-phenylpyrimidinato)iridium(III) (abbreviation: [Ir(tBuppm)₂(acac)]) were deposited by co-evaporation, whereby a first light-emitting layer 1113a (a green light-emitting layer) was formed over the hole-transport layer 1112. The thickness was set to 20 nm and the weight ratio of 2mDBTBPDBq-II to PCBNBB and [Ir(tBuppm)$_2$(acac)] was adjusted to 0.7:0.3:0.05 (=2mDBTBPDBq-II: PCBNBB: [Ir(tBuppm)$_2$(acac)]).

Then, 2mDBTBPDBq-II, PCBNBB, and bis(2,3,5-triphenylpyrazinato)(dipivaloylmethanato)iridium(III) (abbreviation: [Ir(tppr)$_2$(dpm)]) were deposited by co-evaporation, whereby a second light-emitting layer 1113b (a red light-emitting layer) was formed over the first light-emitting layer 1113a. The thickness was set to 5 nm and the weight ratio of 2mDBTBPDBq-II to PCBNBB and [Ir(tppr)$_2$(dpm)] was adjusted to 0.8:0.2:0.05 (=2mDBTBPDBq-II: PCBNBB: [Ir(tppr)$_2$(dpm)]).

Next, 3,5-bis[3-(9H-carbazol-9-yl)phenyl]pyridine (abbreviation: 3,5DCzPPy), 9-phenyl-9H-3-(9-phenyl-9H-carbazol-3-yl)carbazole (abbreviation: PCCP), and tris{2-[5-(2-methylphenyl)-4-(2,6-dimethylphenyl)-4H-1,2,4-triazol-3-yl-κN2]phenyl-κC}iridium(III) (abbreviation: [Ir(mpptz-dmp)$_3$]) were deposited by co-evaporation, whereby a third light-emitting layer 1113c (a blue light-emitting layer) was formed over the second light-emitting layer 1113b. The thickness was set to 30 nm and the weight ratio of 3,5DCzPPy to PCCP and [Ir(mpptz-dmp)$_3$] was adjusted to 0.3:0.7:0.06 (=3,5DCzPPy:PCCP:[Ir(mpptz-dmp)$_3$]).

Next, 3,5DCzPPy was deposited by evaporation to a thickness of 10 nm and then bathophenanthroline (abbreviation: BPhen) was deposited by evaporation to a thickness of 20 nm, so that an electron-transport layer 1114 was formed over the third light-emitting layer 1113c.

Further, an electron-injection layer 1115 was formed over the electron-transport layer 1114 by depositing lithium fluoride (LiF) by evaporation to a thickness of 1 nm.

Lastly, as a second electrode 1103 that functions as a cathode, aluminum was deposited by evaporation to a thickness of 200 nm.

(Comparative Light-Emitting Element 2)

The comparative light-emitting element 2 was fabricated in the same manner as the light-emitting element 1 except for the light-emitting layers (the first light-emitting layer 1113a, the second light-emitting layer 1113b, and the third light-emitting layer 1113c). Hereinafter, a method for forming the light-emitting layers of the comparative light-emitting element 2 will be described.

First, 2mDBTBPDBq-II, PCBNBB, and [Ir(tppr)$_2$(dpm)] were deposited by co-evaporation, whereby the first light-emitting layer 1113a (a red light-emitting layer) was formed over the hole-transport layer 1112. The thickness was set to 10 nm and the weight ratio of 2mDBTBPDBq-II to PCBNBB and [Ir(tppr)$_2$(dpm)] was adjusted to 0.5:0.5:0.05 (=2mDBTBPDBq-II: PCBNBB: [Ir(tppr)$_2$(dpm)]).

Then, 2mDBTBPDBq-II, PCBNBB, and [Ir(tBuppm)$_2$(acac)] were deposited by co-evaporation, whereby the second light-emitting layer 1113b (a green light-emitting layer) was formed over the first light-emitting layer 1113a. The thickness was set to 10 nm and the weight ratio of 2mDBTBPDBq-II to PCBNBB and [Ir(tBuppm)$_2$(acac)] was adjusted to 0.5:0.5:0.05 (=2mDBTBPDBq-II: PCBNBB: [Ir(tBuppm)$_2$(acac)]).

Next, 3,5DCzPPy, PCCP, and [Ir(mpptz-dmp)] were deposited by co-evaporation, whereby the third light-emitting layer 1113c (a blue light-emitting layer) was formed over the second light-emitting layer 1113b. The thickness was set to 30 nm and the weight ratio of 3,5DCzPPy to PCCP and [Ir(mpptz-dmp)$_3$] was adjusted to 0.5:0.5:0.06 (=3,5DCzPPy: PCCP: [Ir(mpptz-dmp)$_3$]).

Note that in all the above evaporation steps, evaporation was performed by a resistance-heating method.

Table 1 shows the element structures of the light-emitting elements of this example, which were fabricated in the above manners.

TABLE 1

| First Electrode | Hole-injection Layer | Hole-transport Layer | Light-emitting Layers | Electron-transport Layer | Electron-injection Layer | Second Electrode |
|---|---|---|---|---|---|---|
| ITSO 110 nm | DBT3P-II:MoO$_x$ (=2:1) 40 nm | PCBNBB 20 nm | * | 3,5DCzPPy 10 nm | Bphen 20 nm | LiF 1 nm | Al 200 nm |

| First Light-emitting Layer | Second Light-emitting Layer | Third Light-emitting Layer |
|---|---|---|
| * Light-emitting Layers of Light-emitting Element 1 | | |
| 2mDBTBPDBq-II:PCBNBB: [Ir(tBuppm)$_2$(acac)] (=0.7:0.3:0.05) 20 nm | 2mDBTBPDBq-II:PCBNBB: [Ir(tppr)$_2$(dpm)] (=0.8:0.2:0.05) 5 nm | 3,5DCzPPy:PCCP: [Ir(mpptz-dmp)$_3$] (=0.3:0.7:0.06) 30 nm |
| * Light-emitting Layers of Comparative Light-emitting Element 2 | | |
| 2mDBTBPDBq-II:PCBNBB: [Ir(tppr)$_2$(dpm)] (=0.5:0.5:0.05) 10 nm | 2mDBTBPDBq-II:PCBNBB: [Ir(tBuppm)$_2$(acac)] (=0.5:0.5:0.05) 10 nm | 3,5DCzPPy:PCCP: [Ir(mpptz-dmp)$_3$] (=0.5:0.5:0.06) 30 nm |

In a glove box containing a nitrogen atmosphere, the light-emitting element 1 and the comparative light-emitting element 2 were sealed with a glass substrate so as not to be exposed to air. Then, operation characteristics of the light-emitting elements of this example were measured. Note that the measurements were carried out at room temperature (in an atmosphere kept at 25° C.).

Figure 9:
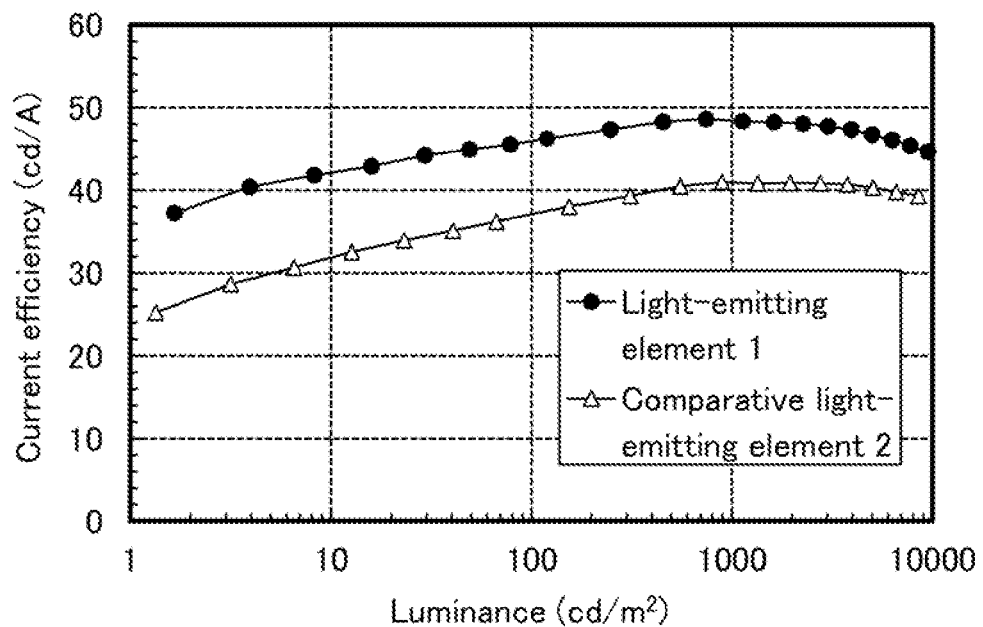
FIG. 9 shows luminance-current efficiency characteristics of light-emitting elements of Example 1.
Figure 10:
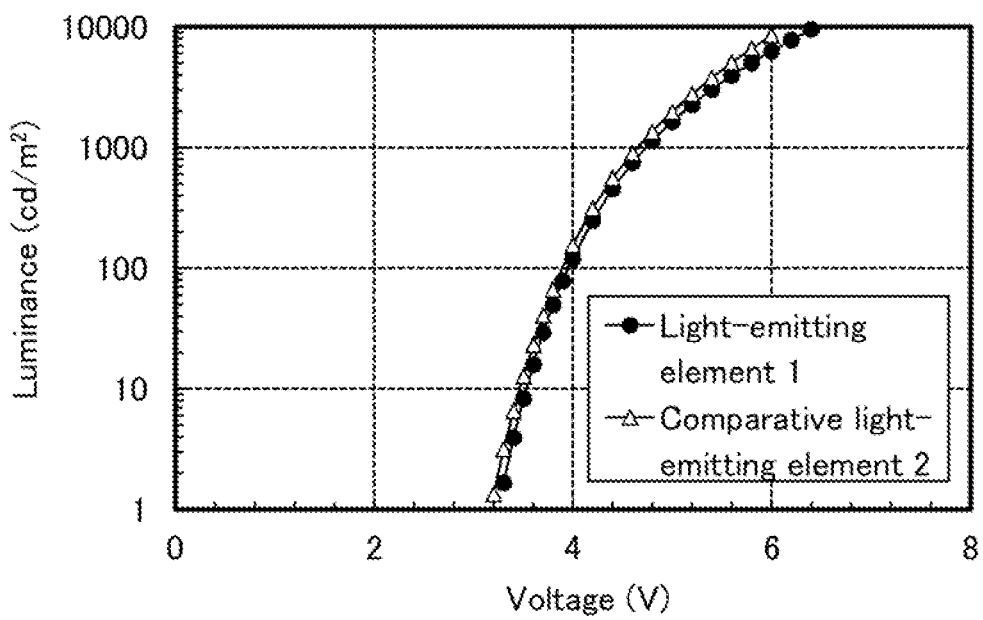
FIG. 10 shows voltage-luminance characteristics of light-emitting elements of Example 1.
Figure 11:
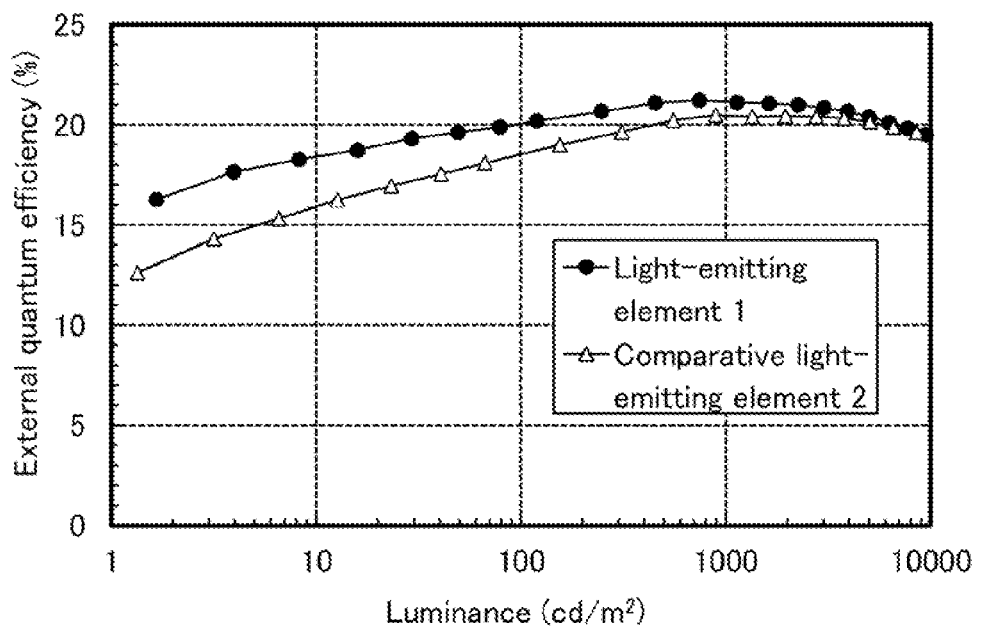
FIG. 11 shows luminance-external quantum efficiency characteristics of light-emitting elements of Example 1.

FIG. 9 shows luminance-current efficiency characteristics of the light-emitting elements of this example. In FIG. 9, the horizontal axis represents luminance (cd/m$^2$) and the vertical axis represents current efficiency (cd/A). FIG. 10 shows voltage-luminance characteristics thereof. In FIG. 10, the horizontal axis represents voltage (V), and the vertical axis represents luminance (cd/m$^2$). FIG. 11 shows luminance-external quantum efficiency characteristics thereof. In FIG. 11, the horizontal axis represents luminance (cd/m$^2$) and the vertical axis represents external quantum efficiency (%). Further, Table 2 shows the voltage (V), current density (mA/cm$^2$), CIE chromaticity coordinates (x, y), current efficiency (cd/A), power efficiency (lm/W), and external quantum efficiency (%) of each light-emitting element of this example at a luminance of 1000 cd/m$^2$.

TABLE 2

| | Voltage (V) | Current Density (mA/cm²) | Chromaticity x | Chromaticity y | Current Efficiency (cd/A) | Power Efficiency (lm/W) | External Quantum Efficiency (%) |
|---|---|---|---|---|---|---|---|
| Light-emitting Element 1 | 4.8 | 2.3 | 0.46 | 0.46 | 48 | 32 | 21 |
| Comparative Light-emitting Element 2 | 4.6 | 2.2 | 0.44 | 0.44 | 41 | 28 | 20 |

From the above, the light-emitting element 1 and the comparative light-emitting element 2 turned out to have excellent element characteristics.

Figure 12:
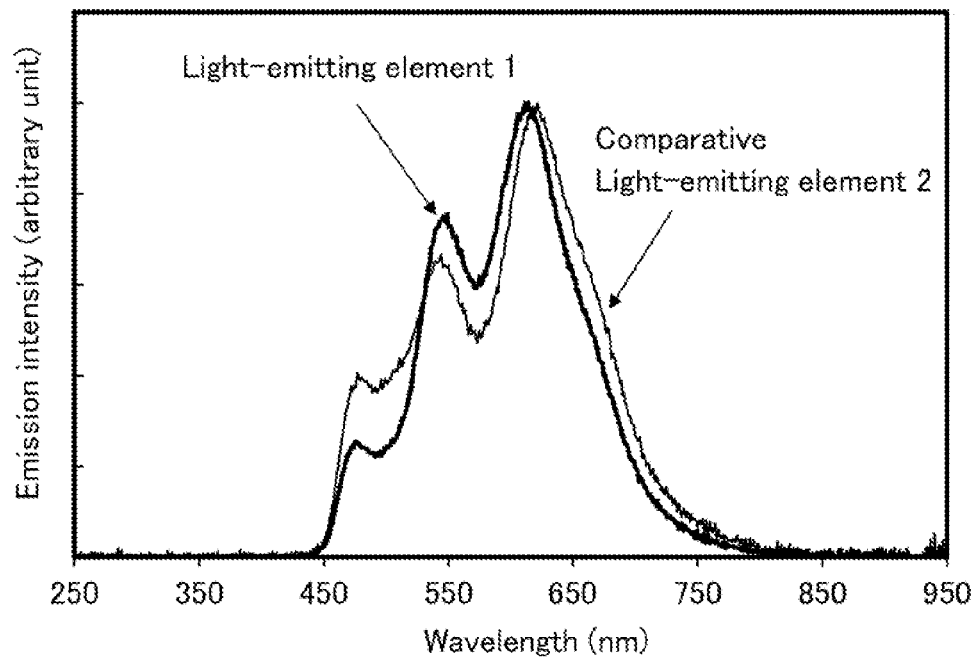
FIG. 12 shows emission spectra of light emitting elements of Example 1

FIG. 12 shows emission spectra of the light-emitting elements of this example. In FIG. 12, the horizontal axis represents a wavelength (nm) and the vertical axis represents emission intensity (arbitrary unit). The CIE chromaticity coordinates of the light-emitting element 1 at a luminance of 1000 cd/m² were (x, y)=(0.46, 0.46). The CIE chromaticity coordinates of the comparative light-emitting element 2 at a luminance of 1000 cd/m² were (x, y)=(0.44, 0.44). As shown in FIG. 12 and Table 2, the light-emitting elements of this example each turned out to exhibit emission spectra that include all of red light derived from [Ir(tppr)$_2$(dpm)], green light derived from [Ir(tBuppm)$_2$(acac)], and blue light derived from [Ir(mpptz-dmp)$_3$]).

Figure 13:
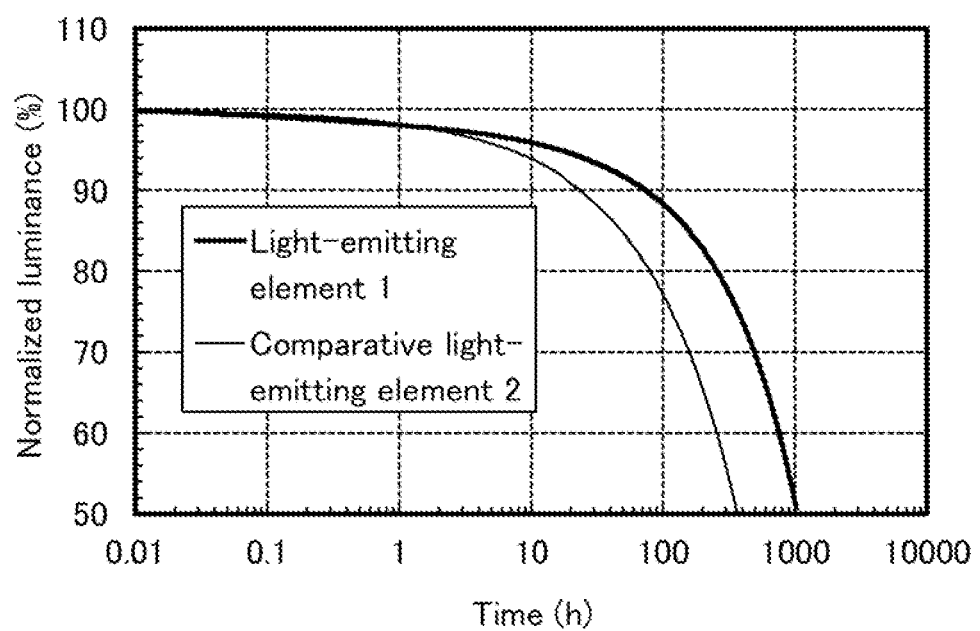
FIG. 13 shows results of reliability tests of light-emitting elements of Example 1.

Next, the light-emitting element 1 and the comparative light-emitting element 2 were subjected to reliability tests. Results of the reliability tests are shown in FIG. 13. In FIG. 13, the vertical axis represents normalized luminance (%) with an initial luminance of 100% and the horizontal axis represents driving time (h) of the element. In the reliability tests, the light-emitting elements of this example were driven at room temperature under the conditions where the initial luminance was set to 3000 cd/m² and the current density was constant. As shown in FIG. 13, the light-emitting element 1 kept 51% of the initial luminance after 1000 hours elapsed in spite of the fact that all light emissions obtained from the light-emitting layers are phosphorescence, which means that the light-emitting element 1 has high durability. Meanwhile, the luminance of the comparative light-emitting element 2 after 370 hours was less than 50% of the initial luminance. These results of the reliability tests revealed that the light-emitting element 1 has a longer lifetime than the comparative light-emitting element 2.

In the comparative light-emitting element 2, because the blue light-emitting layer and the green light-emitting layer are in contact with each other, it is difficult for part of the energy of an exciton in a triplet excited state of [Ir(mpptz-dmp)$_3$] in the blue light-emitting layer that is transferred to a quencher generated in the blue light-emitting layer to be further transferred to a triplet excited state of [Ir(tBuppm)$_2$(acac)] contained in the green light-emitting layer. Meanwhile, in the light-emitting element 1, because the blue light-emitting layer and the red light-emitting layer are in contact with each other, part of the energy of an exciton that is transferred to a quencher generated in the blue light-emitting layer can be transferred to a triplet excited state of [Ir(tppr)$_2$(dpm)] contained in the red light-emitting layer. In the light-emitting element 1, carrier recombination occurs in each of the light-emitting layers and accordingly, light emission can be obtained from each of the phosphorescent compounds contained in the light-emitting layers. This is presumably why the light-emitting element 1 has a longer lifetime than the comparative light-emitting element 2.

The results in this example showed that the light-emitting element 1 of one embodiment of the present invention exhibits favorable element characteristics, has a long lifetime, and provides light from the three kinds of guest materials in a good balance.

Example 21

In this example, a light-emitting element of one embodiment of the present invention will be described with reference to FIG. 8. Chemical formulae of materials used in this example are shown below. Note that the chemical formulae of the materials that are already illustrated are omitted.

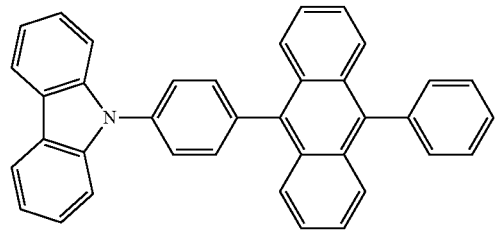

CzPA

A method for fabricating a light-emitting element 3 of this example will be described below.
(Light-Emitting Element 3)

First, the first electrode 1101, the hole-injection layer 1111, and the hole-transport layer 1112 were formed on a glass substrate in the same manner as the light-emitting element 1.

Next, 2mDBTBPDBq-II, PCBNBB, and [Ir(tBuppm)$_2$(acac)] were deposited by co-evaporation, whereby the first light-emitting layer 1113a (a green light-emitting layer) was formed over the hole-transport layer 1112. The thickness was set to 20 nm and the weight ratio of 2mDBTBPDBq-II to PCBNBB and [Ir(tBuppm)$_2$(acac)] was adjusted to 0.8:0.2: 0.05 (=2mDBTBPDBq-II: PCBNBB: [Ir(tBuppm)$_2$(acac)]).

Then, 2mDBTBPDBq-II, PCBNBB, and [Ir(tppr)$_2$(dpm)] were deposited by co-evaporation, whereby the second light-emitting layer 1113b (a red light-emitting layer) was formed over the first light-emitting layer 1113a. The thickness was set to 5 nm and the weight ratio of 2mDBTBPDBq-II to PCBNBB and [Ir(tppr)$_2$(dpm)] was adjusted to 0.8:0.2:0.05 (=2mDBTBPDBq-II: PCBNBB: [Ir(tppr)$_2$(dpm)]).

Next, 3,5DCzPPy, PCCP, and [Ir(mpptz-dmp)$_3$]) were deposited by co-evaporation, whereby the third light-emitting layer 1113c (a blue light-emitting layer) was formed over the second light-emitting layer 1113b. The thickness was set to 30 nm and the weight ratio of 3,5DCzPPy to PCCP and [Ir(mpptz-dmp)$_3$] was adjusted to 0.7:0.3:0.06 (=3,5DCz-PPy: PCCP: [Ir(mpptz-dmp)$_3$]).

Next, 9-[4-(10-phenyl-9-anthryl)phenyl]-9H-carbazole (abbreviation: CzPA) was deposited by evaporation to a thickness of 10 nm and then BPhen was deposited by evaporation to a thickness of 15 nm, so that the electron-transport layer 1114 was formed over the third light-emitting layer 1113c.

Further, the electron-injection layer 1115 was formed over the electron-transport layer 1114 by depositing lithium fluoride (LiF) by evaporation to a thickness of 1 nm.

Lastly, as the second electrode 1103 that functions as a cathode, aluminum was deposited by evaporation to a thickness of 200 nm.

Note that in all the above evaporation steps, evaporation was performed by a resistance-heating method.

Table 3 shows the element structure of the light-emitting element of this example, which was fabricated in the above manner.

TABLE 3

| First Electrode | Hole-injection Layer | Hole-transport Layer | Light-emitting Layers | Electron-transport Layer | Electron-injection Layer | Second Electrode |
|---|---|---|---|---|---|---|
| ITSO 110 nm | DBT3P-II:MoO$_x$ (=2:1) 40 nm | PCBNBB 20 nm | * | CzPA 10 nm | BPhen 15 nm | LiF 1 nm | Al 200 nm |

* Light-emitting Layers of Light-emitting Element 3

| First Light-emitting Layer | Second Light-emitting Layer | Third Light-emitting Layer |
|---|---|---|
| 2mDBTBPDBq-II:PCBNBB:[Ir(tBuppm)$_2$(acac)] (=0.8:0.2:0.05) 20 nm | 2mDBTBPDBq-II:PCBNBB:[Ir(tppr)$_2$(dpm)] (=0.8:0.2:0.05) 5 nm | 3,5DCzPPy:PCCP:[Ir(mpptz-dmp)$_3$] (=0.7:0.3:0.06) 30 nm |

In a glove box containing a nitrogen atmosphere, the light-emitting element 3 was sealed with a glass substrate so as not to be exposed to air. Then, operation characteristics of the element of this example were measured. Note that the measurement was carried out at room temperature (in an atmosphere kept at 25° C.).

Figure 14:
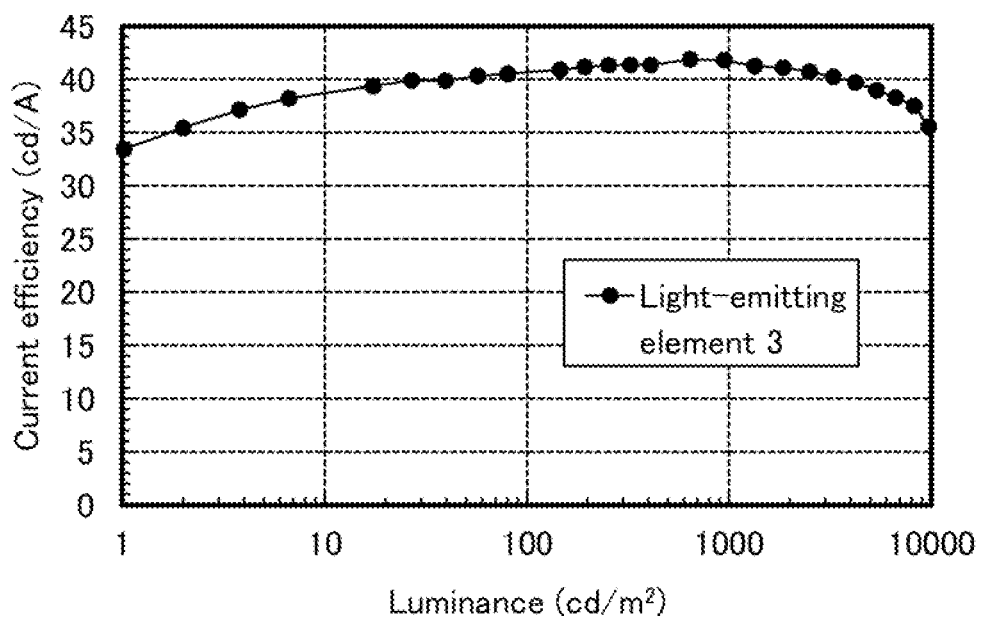
FIG. 14 shows luminance-current efficiency characteristics of a light-emitting element of Example 2
Figure 15:
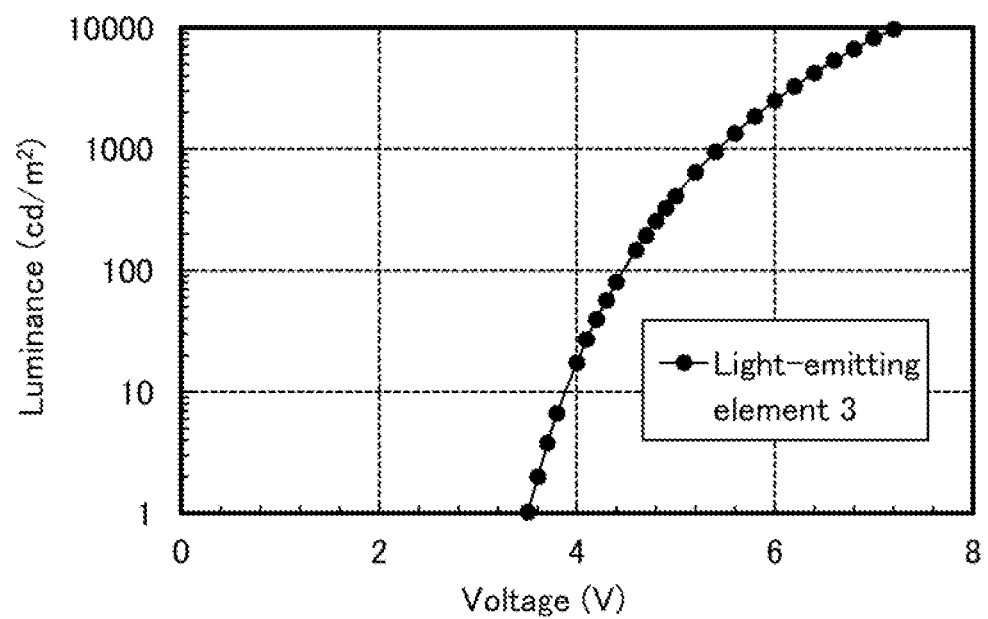
FIG. 15 shows voltage-luminance characteristics of a light-emitting element of Example 2.
Figure 16:
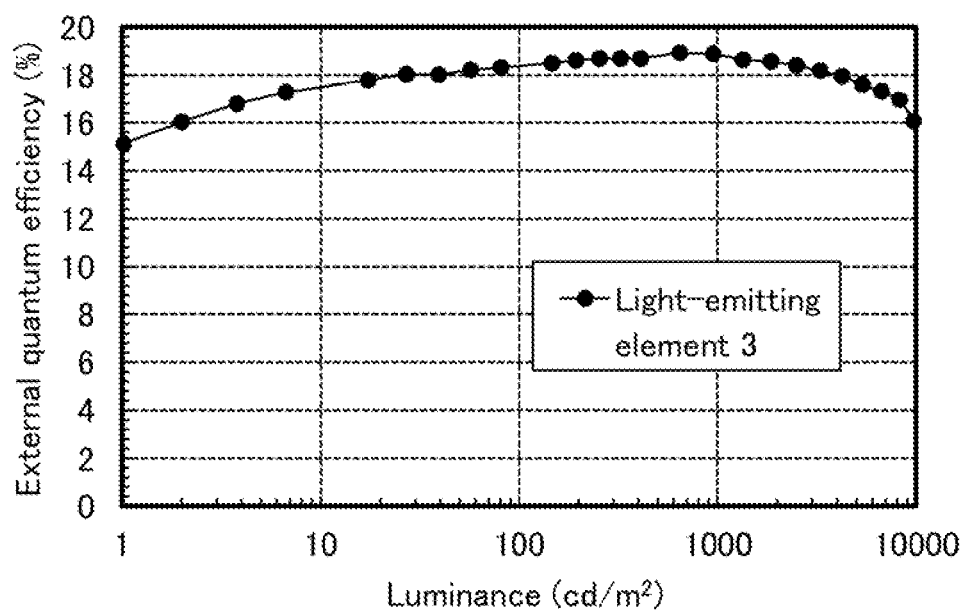
FIG. 16 shows luminance-external quantum efficiency characteristics of a light-emitting element of Example 2.

FIG. 14 shows luminance-current efficiency characteristics of the light-emitting element of this example. In FIG. 14, the horizontal axis represents luminance (cd/m$^2$) and the vertical axis represents current efficiency (cd/A). FIG. 15 shows voltage-luminance characteristics thereof. In FIG. 15, the horizontal axis represents voltage (V), and the vertical axis represents luminance (cd/m$^2$). FIG. 16 shows luminance-external quantum efficiency characteristics thereof. In FIG. 16, the horizontal axis represents luminance (cd/m$^2$) and the vertical axis represents external quantum efficiency (%). Further, Table 4 shows the voltage (V), current density (mA/cm$^2$), CIE chromaticity coordinates (x, y), current efficiency (cd/A), power efficiency (lm/W), and external quantum efficiency (%) of the light-emitting element 3 at a luminance of 1000 cd/m$^2$.

Figure 17:
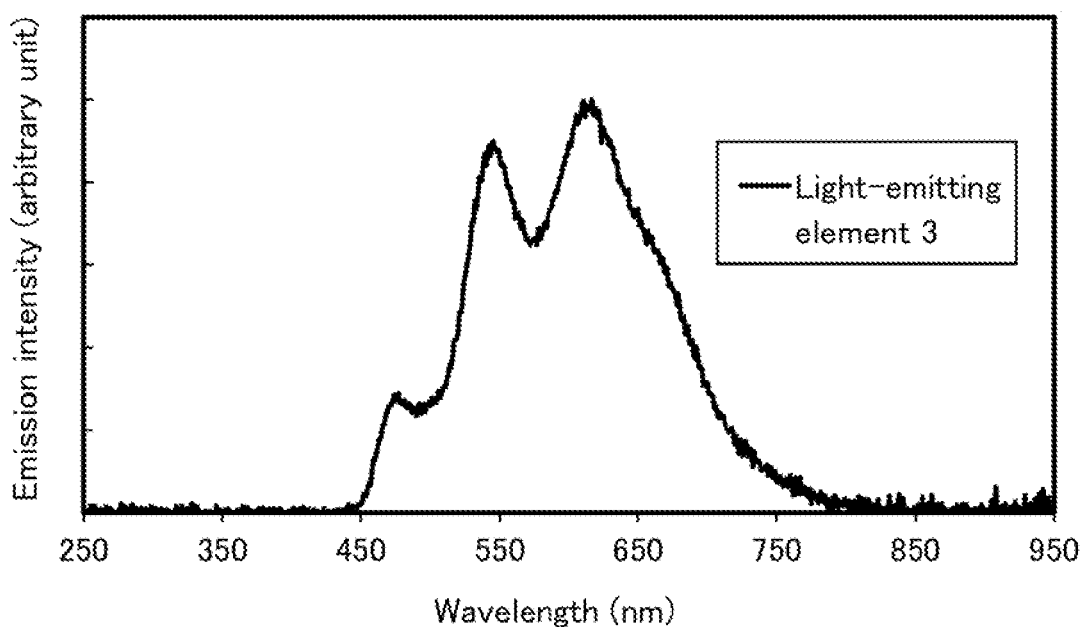
FIG. 17 shows an emission spectrum of a light-emitting element of Example 2.

FIG. 17 shows an emission spectrum of the light-emitting element of this example. In FIG. 17, the horizontal axis represents a wavelength (nm) and the vertical axis represents emission intensity (arbitrary unit). The CIE chromaticity coordinates of the light-emitting element 3 at a luminance of 1000 cd/m$^2$ were (x, y)=(0.46, 0.47). As shown in FIG. 17 and Table 4, the light-emitting element of this example turned out to exhibit an emission spectrum including all of red light derived from [Ir(tppr)$_2$(dpm)], green light derived from [Ir(tBuppm)$_2$(acac)], and blue light derived from [Ir(mpptz-dmp)$_3$].

Figure 18:
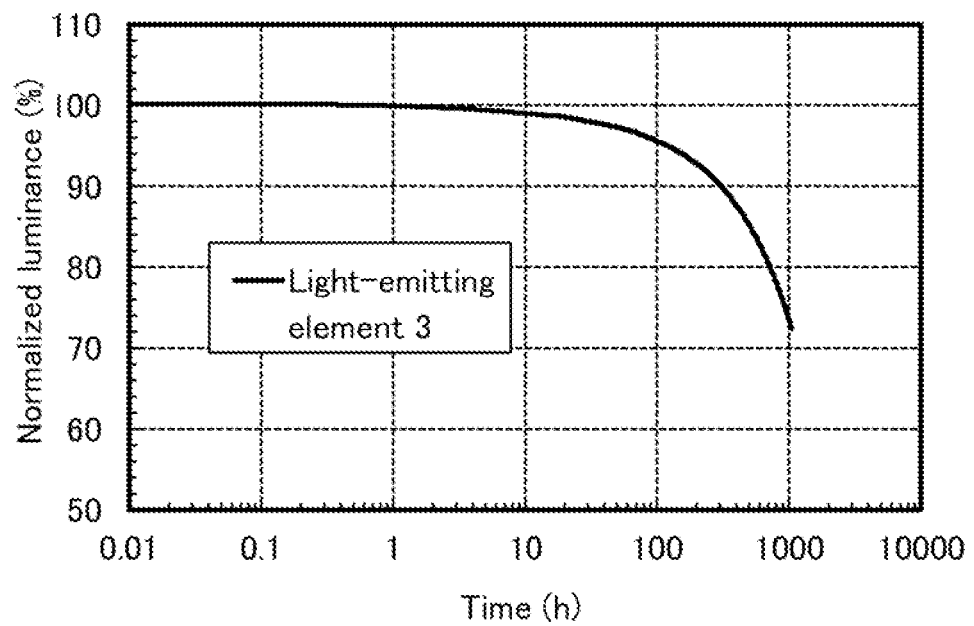
FIG. 18 shows results of a reliability test of a light-emitting element of Example 2.
Figure 19:
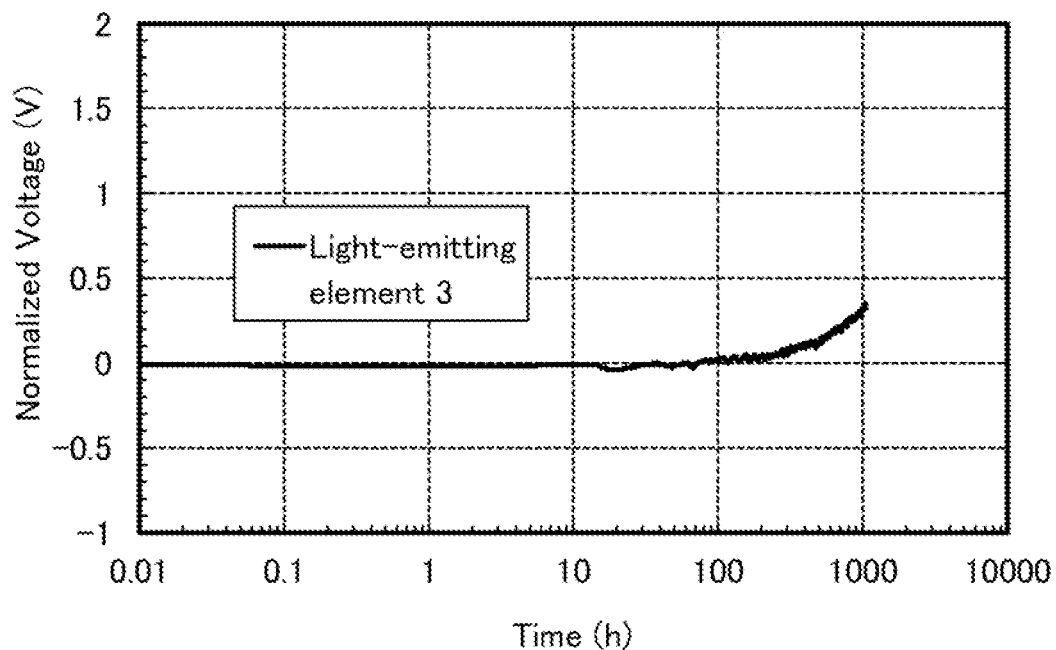
FIG. 19 shows results of a reliability test of a light-emitting element of Example 2.

Next, the light-emitting element 3 was subjected to a reliability test. Results of the reliability test are shown in FIG. 18 and FIG. 19. In FIG. 18, the vertical axis represents normalized luminance (%) with an initial luminance of 100% and the horizontal axis represents driving time (h) of the element. In FIG. 19, the vertical axis represents normalized voltage with an initial voltage of 0 V and the horizontal axis represents driving time (h) of the element. In the reliability test, the light-emitting element of this example was driven at room temperature under the conditions where the initial luminance was set to 3000 cd/m$^2$ and the current density was constant. As shown in FIG. 18, the light-emitting element 3 kept 72% of the initial luminance after 1100 hours elapsed in spite of the fact that all light emissions obtained from the light-emitting layers are phosphorescence. The results of the reliability test revealed that the light-emitting element 3 has a long lifetime. Furthermore, FIG. 19 shows that a voltage increase over driving time of the light-emitting element 3 is small and the light-emitting element 3 has high reliability.

In the electron-transport layer of the light-emitting element 3, CzPA that is a substance with an anthracene skeleton was used for the layer on the anode side, and BPhen that is a π-electron deficient heteroaromatic compound was used for the layer on the cathode side. This structure presumably allowed a voltage increase due to driving to be small in the light-emitting element 3.

TABLE 4

| | Voltage (V) | Current Density (mA/cm$^2$) | Chromaticity x | Chromaticity y | Current Efficiency (cd/A) | Power Efficiency (lm/W) | External Quantum Efficiency (%) |
|---|---|---|---|---|---|---|---|
| Light-emitting Element 3 | 5.4 | 2.3 | 0.46 | 0.47 | 42 | 24 | 19 |

From the above, the light-emitting element 3 turned out to have excellent element characteristics.

The results in this example showed that the light-emitting element 3 of one embodiment of the present invention exhib its favorable element characteristics, has a long lifetime, and provides light from the three kinds of guest materials in a good balance.

Reference Example

A synthesis method of tris{2-[5-(2-methylphenyl)-4-(2,6-dimethylphenyl)-4H-1,2,4-triazol-3-yl-κN2]phenyl-κC}iridium(III) (abbreviation: [Ir(mpptz-dmp)₃]), which was used in the above example, will be described.

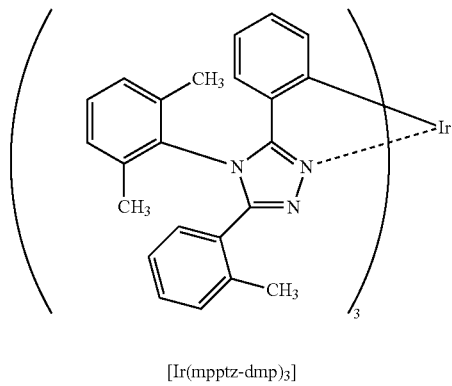

[Ir(mpptz-dmp)₃]

Step 1: Synthesis of N-Benzoyl-N'-2-methylbenzoylhydrazide

First, 15.0 g (110.0 mmol) of benzoylhydrazine and 75 ml of N-methyl-2-pyrrolidinone (NMP) were put into a 300-ml three-neck flask and stirred while being cooled with ice. To this mixed solution, a mixed solution of 17.0 g (110.0 mmol) of o-toluoyl chloride and 15 ml of NMP was slowly added dropwise. After the addition, the mixture was stirred at room temperature for 24 hours. After reaction for the predetermined time, this reacted solution was slowly added to 500 ml of water, so that a white solid was precipitated. The precipitated solid was subjected to ultrasonic cleaning in which water and 1M hydrochloric acid were used alternately. Then, ultrasonic cleaning using hexane was performed, so that 19.5 g of a white solid of N-benzoyl-N'-2-methylbenzoylhydrazide was obtained in a yield of 70%. Synthesis Scheme (a-1) of Step 1 is shown below.

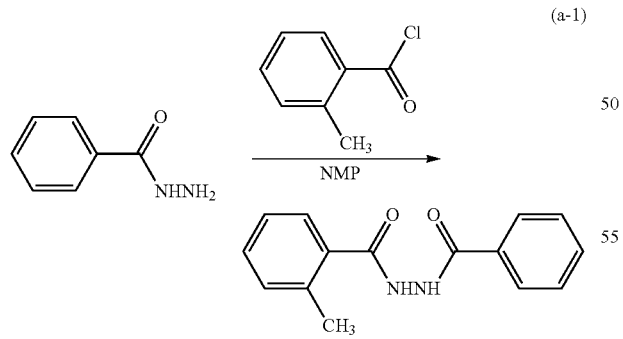

(a-1)

Step 2: Synthesis of [Chloro(2-methylphenyl)methanone][chloro(phenyl)methylidene]hydrazone Next, 12.0 g (47.2 mmol) of N-benzoyl-N'-2-methylbenzoylhydrazide obtained in Step 1 and 200 ml of toluene were put into a 500-ml three-neck flask. To this mixed solution, 19.4 g (94.4 mmol) of phosphorus pentachloride was added and the mixture was heated and stirred at 120° C. for 6 hours. After reaction for the predetermined time, the reacted solution was slowly poured into 200 ml of water and the mixture was stirred for 1 hour. After the stirring, an organic layer and an aqueous layer were separated, and the organic layer was washed with water and a saturated aqueous solution of sodium hydrogen carbonate. After the washing, the organic layer was dried over anhydrous magnesium sulfate. The magnesium sulfate was removed from this mixture by gravity filtration, and the filtrate was concentrated; thus, 12.6 g of a brown liquid of [chloro(2-methylphenyl)methanone][(chloro(phenyl)methylidene]hydrazone was obtained in a yield of 92%. Synthesis Scheme (a-2) of Step 2 is shown below.

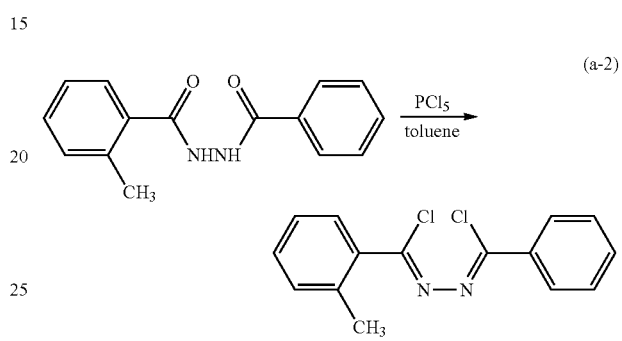

(a-2)

Step 3: Synthesis of 3-(2-Methylphenyl)-4-(2,6-dimethylphenyl)-5-phenyl-4H-1,2,4-triazole (abbreviation: Hmpptz-dmp)

Then, 12.6 g (43.3 mmol) of [chloro(2-methylphenyl)methanone][chloro(phenyl)methylidene]hydrazone obtained in Step 2, 15.7 g (134.5 mmol) of 2,6-dimethylaniline, and 100 ml of N,N-dimethylaniline were put into a 500-ml recovery flask and heated and stirred at 120° C. for 20 hours. After reaction for the predetermined time, this reacted solution was slowly added to 200 ml of 1N hydrochloric acid. Dichloromethane was added to this solution and an objective substance was extracted to an organic layer. The obtained organic layer was washed with water and an aqueous solution of sodium hydrogen carbonate, and was dried over magnesium sulfate. The magnesium sulfate was removed by gravity filtration, and the obtained filtrate was concentrated to give a black liquid. This liquid was purified by silica gel column chromatography. A mixed solvent of ethyl acetate and hexane in a ratio of 1:5 was used as a developing solvent. The obtained fraction was concentrated to give a white solid. This solid was recrystallized with ethyl acetate to give 4.5 g of a white solid of Hmpptz-dmp in a yield of 31%. Synthesis Scheme (a-3) of Step 3 is shown below.

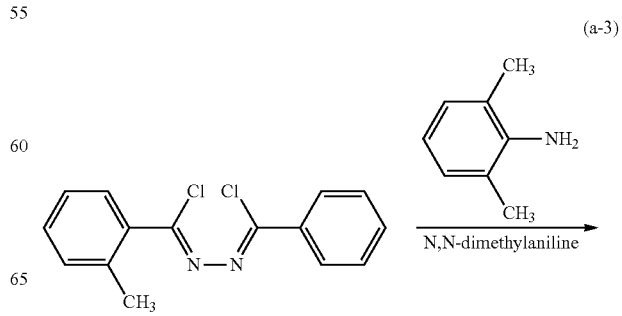

(a-3)

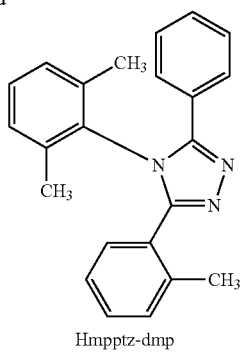

Hmpptz-dmp

Step 4: Synthesis of [Ir(mpptz-dmp)₃]

Then, 2.5 g (7.4 mmol) of Hmpptz-dmp obtained in Step 3 and 0.7 g (1.5 mmol) of tris(acetylacetonato)iridium(III) were put into a container for high-temperature heating, and degasification was carried out. The mixture in the reaction container was heated and stirred at 250° C. for 48 hours under Ar flow. After reaction for the predetermined time, the obtained solid was washed with dichloromethane, and an insoluble green solid was obtained by suction filtration. This solid was dissolved in toluene and filtered through a stack of alumina and Celite (produced by Wako Pure Chemical Industries, Ltd., Catalog No. 531-16855). The obtained fraction was concentrated to give a green solid. This solid was recrystallized with toluene, so that 0.8 g of a green powder was obtained in a yield of 45%. Synthesis Scheme (a-4) of Step 4 is shown below.

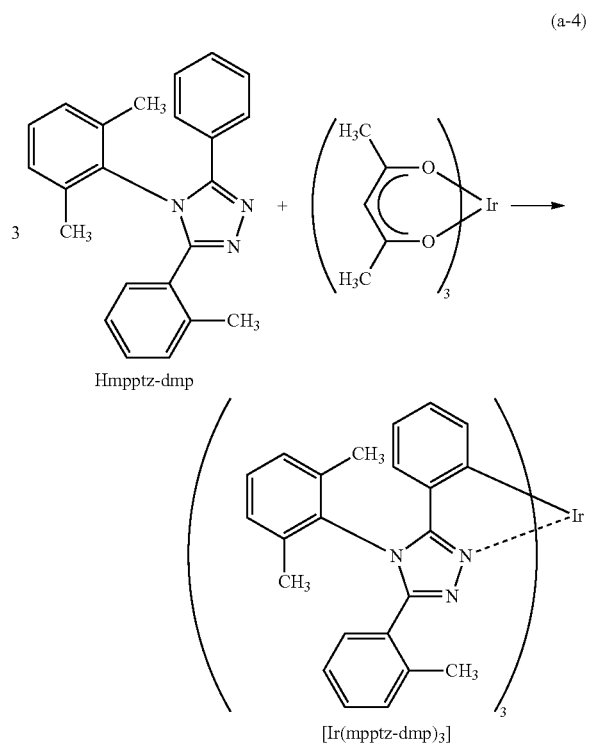

(a-4)

Analysis results by nuclear magnetic resonance ($^1$H NMR) spectroscopy of the green powder obtained in Step 4 is described below. The results revealed that [Ir(mpptz-dmp)₃] was obtained.

$^1$H NMR, δ (toluene-$d_s$): 1.82 (s, 3H), 1.90 (s, 3H), 2.64 (s, 3H), 6.56-6.62 (m, 3H), 6.67-6.75 (m, 3H), 6.82-6.88 (m, 1H), 6.91-6.97 (t, 1H), 7.00-7.12 (m, 2H), 7.63-7.67 (d, 1H).

This application is based on Japanese Patent Application serial no. 2013-104880 filed with Japan Patent Office on May 17, 2013, the entire contents of which are hereby incorporated by reference.

What is claimed is:

1. A light-emitting element comprising:
   a first electrode:
   a first light-emitting layer over the first electrode, the first light-emitting layer comprising a first phosphorescent compound and a first host material;
   a second light-emitting layer over the first light-emitting layer, the second light-emitting layer comprising a second phosphorescent compound and a second host material;
   a third light-emitting layer over the second light-emitting layer, the third light-emitting layer comprising a third phosphorescent compound and a third host material; and
   a second electrode over the third light-emitting layer,
   wherein between a peak of an emission spectrum of the first phosphorescent compound, a peak of an emission spectrum of the second phosphorescent compound, and a peak of an emission spectrum of the third phosphorescent compound, the peak of the emission spectrum of the second phosphorescent compound is on a longest wavelength side and the peak of the emission spectrum of the third phosphorescent compound is on a shortest wavelength side, and
   wherein the third host material has higher triplet excitation energy than the first host material and the second host material.

2. The light-emitting element according to claim 1,
   wherein the first phosphorescent compound emits green light,
   wherein the second phosphorescent compound emits red light, and
   wherein the third phosphorescent compound emits blue light.

3. The light-emitting element according to claim 1,
   wherein the first host material, the second host material, and the third host material each have an electron-transport property when the first electrode functions as an anode.

4. The light-emitting element according to claim 1,
   wherein the first host material, the second host material, and the third host material each have a hole-transport property when the first electrode functions as a cathode.

5. The light-emitting element according to claim 1,
   wherein the first host material, the second host material, and the third host material each have a hole-transport property and an electron-transport property, and
   wherein the first host material, the second host material, and the third host material each comprise a hole-transport skeleton and an electron-transport skeleton.

6. The light-emitting element according to claim 1,
   wherein the first host material is the same as the second host material.

7. The light-emitting element according to claim 1,
   wherein the first light-emitting layer comprises a first carrier-transport compound, wherein one of the first host material and the first carrier-transport compound has a hole-transport property,
wherein the other of the first host material and the first carrier-transport compound has an electron-transport property,
wherein the second light-emitting layer comprises a second carrier-transport compound,
wherein one of the second host material and the second carrier-transport compound has a hole-transport property,
wherein the other of the second host material and the second carrier-transport compound has an electron-transport property,
wherein the third light-emitting layer comprises a third carrier-transport compound,
wherein one of the third host material and the third carrier-transport compound has a hole-transport property, and
wherein the other of the third host material and the third carrier-transport compound has an electron-transport property.

8. The light-emitting element according to claim 1,
wherein the second light-emitting layer has a thickness greater than or equal to 2 nm and less than or equal to 20 nm.

9. The light-emitting element according to claim 1,
wherein the second light-emitting layer is in contact with the first light-emitting layer and the third light-emitting layer.

10. A lighting device comprising the light-emitting element according to claim 1.

11. An electronic device comprising a light-emitting device, the light-emitting device comprising:
the light-emitting element according to claim 1; and
a unit for controlling the light-emitting element.

12. A light-emitting element comprising:
a first electrode;
a first light-emitting layer over the first electrode, the first light-emitting layer comprising a first phosphorescent compound and a first host material;
a second light-emitting layer over the first light-emitting layer, the second light-emitting layer comprising a second phosphorescent compound and a second host material;
a third light-emitting layer over the second light-emitting layer, the third light-emitting layer comprising a third phosphorescent compound and a third host material; and
a second electrode over the third light-emitting layer,
wherein the first phosphorescent compound emits green light,
wherein the second phosphorescent compound emits red light, and
wherein the third phosphorescent compound emits blue light.

13. The light-emitting element according to claim 12,
wherein the first host material, the second host material, and the third host material each have an electron-transport property when the first electrode functions as an anode.

14. The light-emitting element according to claim 12,
wherein the first host material, the second host material, and the third host material each have a hole-transport property when the first electrode functions as a cathode.

15. The light-emitting element according to claim 12,
wherein the first host material, the second host material, and the third host material each have a hole-transport property and an electron-transport property, and wherein the first host material, the second host material, and the third host material each comprise a hole-transport skeleton and an electron-transport skeleton.

16. The light-emitting element according to claim 12,
wherein the first host material is the same as the second host material.

17. The light-emitting element according to claim 12,
wherein the first light-emitting layer comprises a first carrier-transport compound,
wherein one of the first host material and the first carrier-transport compound has a hole-transport property,
wherein the other of the first host material and the first carrier-transport compound has an electron-transport property,
wherein the second light-emitting layer comprises a second carrier-transport compound,
wherein one of the second host material and the second carrier-transport compound has a hole-transport property,
wherein the other of the second host material and the second carrier-transport compound has an electron-transport property,
wherein the third light-emitting layer comprises a third carrier-transport compound,
wherein one of the third host material and the third carrier-transport compound has a hole-transport property and
wherein the other of the third host material and the third carrier-transport compound has an electron-transport property.

18. The light-emitting element according to claim 12,
wherein the second light-emitting layer has a thickness greater than or equal to 2 nm and less than or equal to 20 nm.

19. The light-emitting element according to claim 12,
wherein the second light-emitting layer is in contact with the first light-emitting layer and the third light-emitting layer.

20. A lighting device comprising the light-emitting element according to claim 12.

21. An electronic device comprising a light-emitting device, the light-emitting device comprising:
the light-emitting element according to claim 12; and
a unit for controlling the light-emitting element.

22. A light-emitting element comprising:
a first electrode;
a first light-emitting layer over the first electrode, the first light-emitting layer comprising a first phosphorescent compound and a first host material;
a second light-emitting layer over the first light-emitting layer, the second light-emitting layer comprising a second phosphorescent compound and a second host material;
a third light-emitting layer over the second light-emitting layer, the third light-emitting layer comprising a third phosphorescent compound and a third host material, and
a second electrode over the third light-emitting layer,
wherein the second phosphorescent compound emits red light,
wherein the third phosphorescent compound emits blue light, and
wherein the second light-emitting layer and the third light-emitting layer are in contact with each other.

23. The light-emitting element according to claim 22,
wherein the first host material, the second host material, and the third host material each have an electron-transport property when the first electrode functions as an anode.

24. The light-emitting element according to claim 22,
wherein the first host material, the second host material, and the third host material each have a hole-transport property when the first electrode functions as a cathode.

25. The light-emitting element according to claim 22,
wherein the first host material, the second host material, and the third host material each have a hole-transport property and an electron-transport property, and
wherein the first host material, the second host material, and the third host material each comprise a hole-transport skeleton and an electron-transport skeleton.

26. The light-emitting element according to claim 22,
wherein the first host material is the same as the second host material.

27. The light-emitting element according to claim 22,
wherein the first light-emitting layer comprises a first carrier-transport compound,
wherein one of the first host material and the first carrier-transport compound has a hole-transport property,
wherein the other of the first host material and the first carrier-transport compound has an electron-transport property,
wherein the second light-emitting layer comprises a second carrier-transport compound,
wherein one of the second host material and the second carrier-transport compound has a hole-transport property,
wherein the other of the second host material and the second carrier-transport compound has an electron-transport property,
wherein the third light-emitting layer comprises a third carrier-transport compound,
wherein one of the third host material and the third carrier-transport compound has a hole-transport property, and
wherein the other of the third host material and the third carrier-transport compound has an electron-transport property.

28. The light-emitting element according to claim 22,
wherein the second light-emitting layer has a thickness greater than or equal to 2 nm and less than or equal to 20 nm.

29. A lighting device comprising the light-emitting element according to claim 22.

30. An electronic device comprising a light-emitting device, the light-emitting device comprising:
the light-emitting element according to claim 22; and
a unit for controlling the light-emitting element.

* * * * *